(12) United States Patent
Xiao et al.

(10) Patent No.: US 9,758,780 B2
(45) Date of Patent: Sep. 12, 2017

(54) WHOLE GENOME MAPPING BY DNA SEQUENCING WITH LINKED-PAIRED-END LIBRARY

(71) Applicants: Ming Xiao, Huntingdon Valley, PA (US); Justin Sibert, Philadelphia, PA (US)

(72) Inventors: Ming Xiao, Huntingdon Valley, PA (US); Justin Sibert, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 90 days.

(21) Appl. No.: 14/728,223

(22) Filed: Jun. 2, 2015

(65) Prior Publication Data
US 2015/0344873 A1 Dec. 3, 2015

Related U.S. Application Data

(60) Provisional application No. 62/006,504, filed on Jun. 2, 2014.

(51) Int. Cl.
*C12Q 1/68* (2006.01)
*C12N 15/10* (2006.01)
*C07H 21/02* (2006.01)
*G06F 19/18* (2011.01)

(52) U.S. Cl.
CPC ....... *C12N 15/1068* (2013.01); *C12Q 1/6806* (2013.01); *G06F 19/18* (2013.01)

(58) Field of Classification Search
CPC .... C12N 15/1068; C12Q 1/6806; G06F 19/18
See application file for complete search history.

(56) References Cited

U.S. PATENT DOCUMENTS

| | | | |
|---|---|---|---|
| 2012/0231508 | A1 | 9/2012 | Chiu et al. |
| 2012/0245037 | A1 | 9/2012 | Hogers et al. |
| 2013/0177902 | A1 | 7/2013 | Xiao et al. |
| 2013/0240357 | A1 | 9/2013 | Xiao et al. |

OTHER PUBLICATIONS

Joneja, A. et al., Anal. Biochem., vol. 414, pp. 58-69 (2011).*

(Continued)

*Primary Examiner* — Teresa Strzelecka
(74) *Attorney, Agent, or Firm* — Saul Ewing LLP; Kathryn Doyle

(57) ABSTRACT

The present invention relates to innovative means of generating sequence-linked DNA fragments and subsequent uses of such linked DNA fragments for de novo haplotype-resolved whole genome mapping and massively parallel sequencing. In various embodiments described herein, the methods of the invention relate to methods of generating paired-end nucleic acid fragment sharing common linker nucleic acid sequences using a nicking endonuclease, a T7 endonuclease, a restriction enzyme, or a transposase, methods of analyzing the nucleotides sequences from the linked-paired-end sequenced fragments, and methods of de novo whole genome mapping. Thus, the methods of this invention allow establishing sequence contiguity across the whole genome, and achieving high-quality, low-cost de novo assembly of complex genomes.

16 Claims, 32 Drawing Sheets

(56) References Cited

OTHER PUBLICATIONS

Church, et al., "Lineage-specific biology revealed by a finished genome assembly of the mouse", PLoS Biol. 7(5), May 5, 2009, e1000112.
Kidd, et al., "Mapping and sequencing of structural variation from eight human genomes", Nature 453(7191), May 1, 2008, 56-64.
Lam, et al., "Genome mapping on nanochannel arrays for structural variation analysis and sequence assembly", Nat Biotechnol. 30(8), Aug. 2012, 771-776.
Latreille, et al., "Optical mapping as a routine tool for bacterial genome sequence finishing", BMC Genomics. 8:321, Sep. 14, 2007, doi:10.1186/1471-2164-8-321.
Teague, et al., "High-resolution human genome structure by single-molecule analysis", Proc Natl Acad Sci U S A. 107(24), Jun. 15, 2010, 10848-10853.
Wu, et al., "Optical mapping of the *Mycobacterium avium* subspecies paratuberculosis genome.", BMC Genomics. 10:25, Jan. 15, 2009, doi: 10.1186/1471-2164-10-25.
Zhou, et al., "A single molecule scaffold for the maize genome", PLoS Genet. 5(11), Nov. 2009, e1000711.
Zhou, et al., "Validation of rice genome sequence by optical mapping", BMC Genomics. 8:278, Aug. 15, 2007, doi:10.1186/1471-2164-8-278.

\* cited by examiner

Nicking-Flap-T7 Endonuclease Scheme for Creating Linker-Sequence

Step 1 and 2: nicking top strand with Nb.Bbvcl (GCTGAGG), and displace down stream strand

SEQ ID NO: 5

TTTCCCAAATTTCCCGGGTTTCCCAAAGGGCTGAGGTTTAAAGGGTTTCCCGGGAAGGGCCCTTT
AAAGGGTTTAAAGGGCCCAAAGGGTTTCCCGACTCCGAAATTTCCCAAAGGGCCCTTCCCGGGAAA

SEQ ID NO: 6

Step 3: cutting the opposite strand across the nicking site

TTTCCCAAATTTCCCGGGTTTCCCAAAGGGCTGAGGTTAAAGGGTTTCCCGGGAA
AAAGGGTTTAAAGGGCCCAAAGGGTTTCCCGACTCCAAATTTCCCAAAGGGCCCTT

TGAGGTTTAAAGGGTTTCCCGGGAAGGGCCCTTT
                      CCCGGGAAA

Step 4: fill in the 5' overhang, and two fragments share the end sequences

TGAGGTTTAAAGGGTTTCCCGGGAA

TTTCCCAAATTTCCCGGGTTTCCCAAAGGGCTGAGGTTTAAAGGGTTTCCCGGGAA
AAAGGGTTTAAAGGGCCCAAAGGGTTTCCCGACTCCAAATTTCCCAAAGGGCCCTT

TGAGGTTAAAGGGTTTCCCGGGAAAGGGCCCTTT
ATCCCAAATTTCCCAAAGGGCCCTTTCCCGGGAAA

FIG. 10

Break the long single DNA fragments
Each end of the DNA fragments share the same
50-100 base pairs with downstream fragments

Construct paired-end library by circularizing the fragments

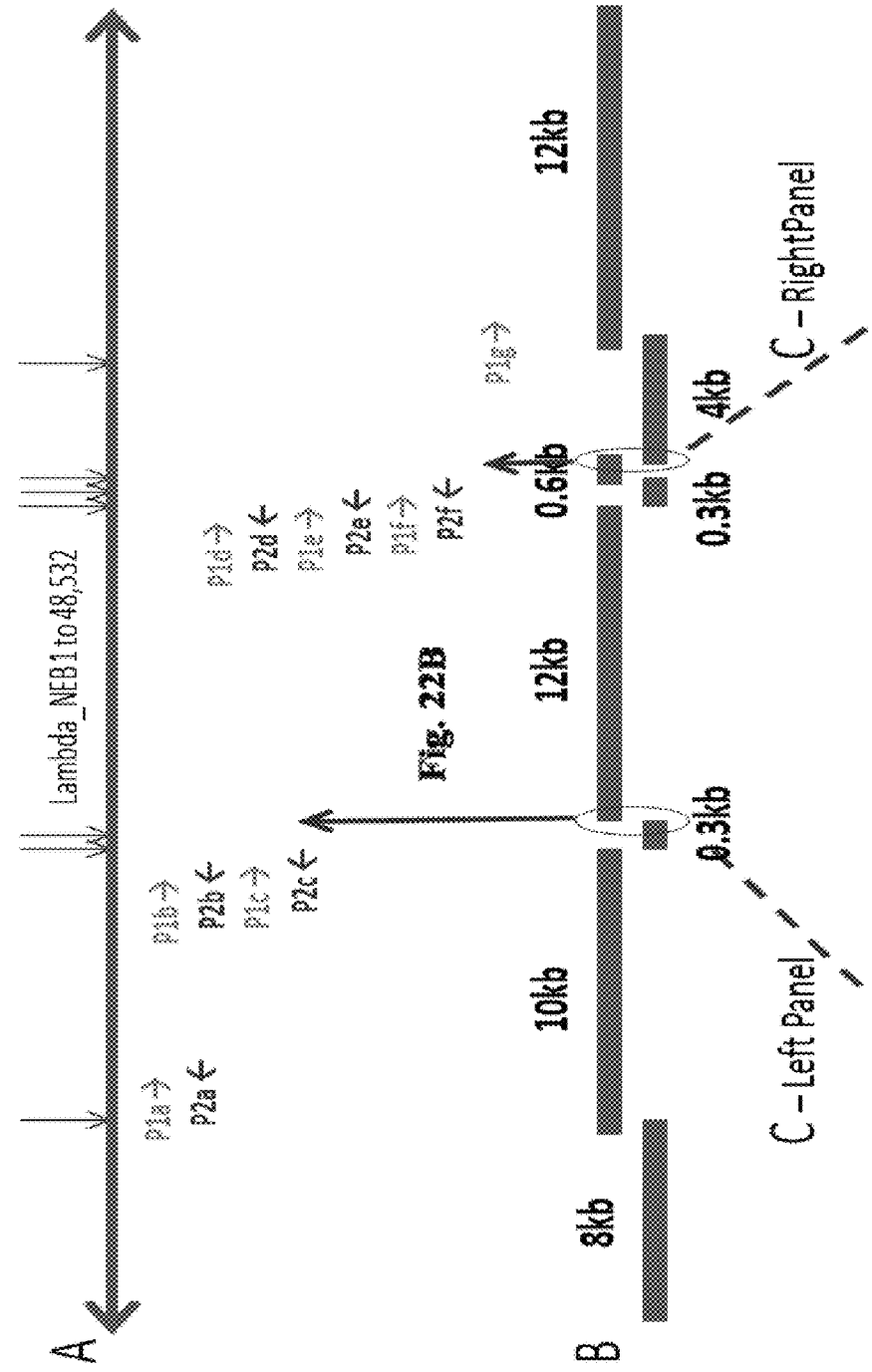

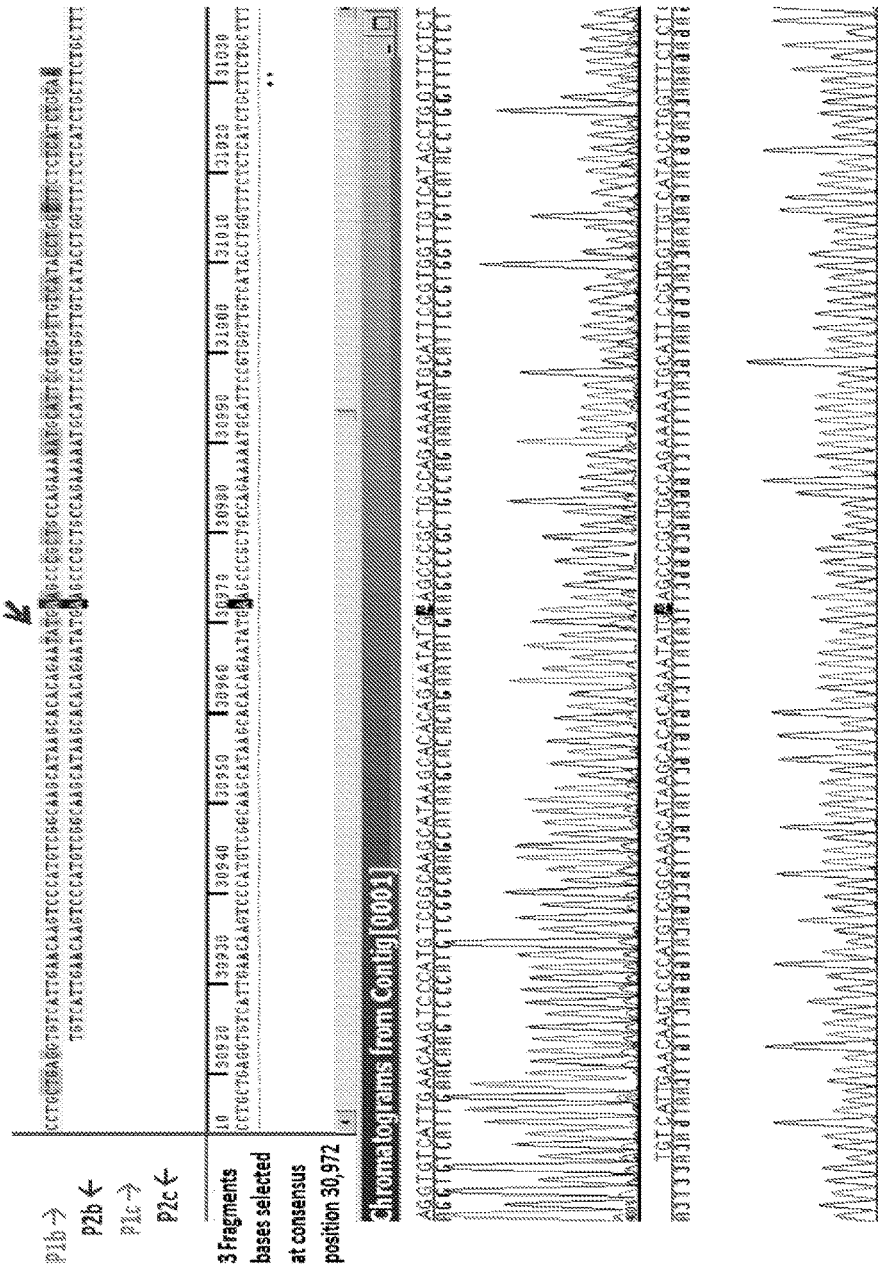

(right panel)

Uniqueness of shared sequences in MHC region (method 2)

- Number of Nicking sites: 3,202

|  |  |  | Shared Sequence Length (bp) | | | |
|---|---|---|---|---|---|---|
|  |  |  | 57 | 107 | 157 | 207 |
| Error Tolerance | Exact Match | # of Unique | 2,615 (81.7%) | 3,173 (99.1%) | 3,183 (99.4%) | 3,187 (99.5%) |
|  |  | Average occurrence | 21.6 | 2.0 | 1.2 | 0.8 |
|  | <= 1 Mismatch | # of Unique | 2,055 (64.2%) | 3,138 (98.0%) | 3,173 (99.1%) | 3,180 (99.3%) |
|  |  | Average occurrence | 183.1 | 3.7 | 2.2 | 1.4 |

FIG. 24

Haplotype analysis of human major histocompatibility complex region

Number of nicking sites (linkers): 3,202  
Number of SNPs: 128,923

MHC region size: 4,795,374

|  | Linker length (bp) | | | |
| --- | --- | --- | --- | --- |
|  | 57 | 107 | 157 | 207 |
| Number of linkers that contain one or more SNPs | 1,798 | 2,464 | 2,763 | 3,002 |
| Number of linkers that contain ≥ 1 SNP and next to another linker that contains ≥ 1 SNP | 1,497 | 2,325 | 2,711 | 2,988 |
| Number of haplotype blocks with all nicking site combinations | 11 (covering 4,524,161bp, i.e., 94.34% of MHC region) | 4 (covering 4,721,844bp, i.e., 98.47% of MHC region) | 3 (covering 4,747,388bp, i.e., 99.00% of MHC region) | 2 (covering 4,769,936bp, i.e., 99.47% of MHC region) |

FIG. 26

Workflow

Linker-Sequence generation
1. Nick with Nb.BbvCI
2. Flap with Klenow exo-
3. Nick with Nt.BbvcI
4. Hexamer+ Ecoli polymerase I fill the single stranded 3' overhang
5. Tag ligase to seal the nick
6. QiaEX II to clean up (different lengths with different protocols?)

Paired-end Sequence Library construction
7. Blunting with Biotin-dNTP (or ligate with biotinlated oligos)
8. QiaEX II clean up
9. **************Gel size selection QiaEX II clean
10. Circularization
11. Fragmentation and size selection
12. Adaptor ligation (fragment size and sequencing)
13. Sequencing Map assembly Data analysis
14. Map assembly
15. De novo genome assembly, haplotype and structural variation analysis

FIG. 27A

WHOLE GENOME MAPPING BY DNA SEQUENCING WITH LINKED-PAIRED-END LIBRARY

CROSS-REFERENCE TO RELATED APPLICATIONS

The present application claims priority under 35 U.S.C. §119(e) to U.S. Provisional Application No. 62/006,504, filed Jun. 2, 2014, which application is hereby incorporated by reference in its entirety herein.

STATEMENT REGARDING FEDERALLY SPONSORED RESEARCH OR DEVELOPMENT

This invention was made with government support under grants R21HG007205 and R01HG005946, awarded by National Institute of Health. The government has certain rights in the invention.

BACKGROUND OF THE INVENTION

Genomics holds much promise for huge improvements in human healthcare. Despite major advances in high-throughput sequencing, genomics faces several practical challenges. Accurate de novo genome assembly of sequence reads and structural variant analysis using "short read" shotgun sequencing remain challenging and represent the weak link in genome projects (Blakesley, et al. BMC Genomics 11: 21, 2010; Chain, et al. Science 326: 236-237, 2009). Most re-sequencing projects rely on mapping the sequencing data to the reference sequence to identify variants of interest (Ley et al., Nature 456, 66-72, 2008). When whole genome assembly is attempted, it is done by paired-end sequencing of cloned genomic DNA fragments to provide scaffolds for assembly (Siegel et al., Genomics 68, 237-246, 2000). Cloning of large DNA fragments is difficult. Therefore small insert libraries of varying sizes have been prepared for paired-end sequencing, thus limiting the resolution of haplotypes and increasing the complexity, time, and cost of the sequencing project. In addition, complex genomic loci, such as the major histocompatibility (MHC) region, are important for infectious and autoimmune diseases (Fernando et al., PLoS Genet 4, e1000024, 2008). These regions contain highly repetitive sequences and are particularly challenging for sequence assembly. As such, robust technologies that can aid in de novo sequence assembly are sorely needed as whole genome sequencing becomes more widely adopted.

Emerging whole genome scanning techniques reveal the prevalence and importance of structural variation. Detecting copy number variation often relies on detection of relative signal intensities by array-based or quantitative PCR-based technologies. Array-based methods, such as array-based comparative genomic hybridization (aCGH), have been used extensively in interrogation of copy number variation in the human genome (Sebat et al., Science 305, 525-528, 2004; Iafrate et al., Genet 36, 949-951, 2004). Except for deletions, however, these methods do not provide positional information regarding the locations of copy number variants (CNVs) and cannot detect balanced structural variation, such as inversions or translocations (Carter, Nat Genet 39(7 Suppl): S16-21, 2007). Paired-end mapping techniques, traditionally by Sanger sequencing and now by next-generation sequencing (Medvedev et all., Nat Meth 6, S13-S20, 2009), generally have low sensitivity in repetitive regions, where most of the structural variation lies (Feuk et al., Rev Genet 7, 85-97, 2006). Recent efforts to characterize CNVs in human genomes at high resolution involve paired-end mapping of clones, but this approach, while useful for exploratory studies in this small sample set, is too labor-intensive and time-consuming to be applicable for analysis of large numbers of individuals. Furthermore the resolution is no better than 8 kb (Kidd et al., Nature 453, 56-64, 2008).

Restriction mapping was instrumental in the Human Genome Project. One approach to address drawbacks of traditional restriction mapping is optical mapping (Jing et al., Proceedings of the National Academy of Sciences 95, 8046-8051, 1998). In this approach, large DNA fragments are stretched and immobilized on glass slides and cut in situ with restriction enzymes. Optical mapping was used to construct ordered restriction maps for whole genomes (Zhou et al., BMC Genomics 8, 278, 2007; Zhou et al. PLoS Genet 5, e1000711, 2009; Church et al., PLoS Biol 7, e1000112, 2009; Teague et al., PNAS 107, 10848-10853) and it provided scaffolds for shotgun sequence assembly and validation (Wu et al., BMC Genomics 10, 25, 2009; Latreille et al., BMC Genomics 8, 321, 2007). This method, however, is limited by its low throughput, non-uniform DNA stretching, imprecise DNA length measurement, and high error rates.

Therefore despite all developments in high throughput sequencing, there remains a need art for method of sequencing the whole genome with great accuracy, low cost and within a reasonable timeline.

SUMMARY OF THE INVENTION

The present invention provides a method of generating a linked-paired-end nucleic acid fragment from a DNA sample. The method comprises (a) contacting a double-stranded DNA template having a first and a second DNA strand with a first nicking endonuclease to form a nick at a sequence-specific nicking location on the first DNA strand; (b) conducting a base extension reaction on the first DNA strand along a corresponding region of the second DNA strand thereby forming a single-stranded flap on the double-stranded DNA template adjacent to the sequence-specific nicking location; (c) contacting the double-stranded DNA template of (b) with a second nicking endonuclease to form a cut at a sequence-specific location thereby generating two cut DNA fragments wherein the single stranded flap of (b) can hybridize on the complementary strand of one of the two fragments of the cut DNA; and (d) conducting a base extension reaction on the second DNA strand of the other fragment of the cut DNA of (c) along a corresponding region of the first DNA strand, wherein the reaction starts at the nick and progressing toward the 3' end of the first DNA strand thereby generating a double-stranded DNA fragment that shares common linker sequences with the double-stranded DNA fragment of (c).

In another aspect, the present invention provides a method of generating a linked-paired-end nucleic acid fragment from a DNA sample. The method comprises (a) contacting a double-stranded DNA template having a first and a second DNA strand with a first nicking endonuclease to form a nick at a sequence-specific nicking location on the first DNA strand; (b) conducting a base extension reaction on the first DNA strand along a corresponding region of the second DNA strand thereby forming a single-stranded flap on the double-stranded DNA template adjacent to the sequence-specific nicking location; (c) contacting the double-stranded DNA template of (b) with a second nicking endonuclease being a T7 endonuclease to generate a cut of the second DNA strand across the nicking sites thereby generating two cut DNA fragments: a first fragment with a blunt end and a second fragment with an overhang corresponding to the single stranded flap of (b); and (d) conducting a base extension reaction on the second fragment with the flap overhang from (c) wherein the based extension being along the corresponding region of the single stranded flap, and the reaction starting at the nick site of the T7 endonuclease and progressing toward the end of the stranded flap thereby generating a blunt end double-stranded DNA fragment that shares common linker sequences with the first double-stranded DNA fragment of (c).

In some embodiments, the generated DNA fragments of (d) are further processed further using hexamer extension. In some embodiments, the first and second nicking endonucleases are type II endonucleases. In other embodiments, the first and second nicking endonucleases comprise one or more endonucleases selected from the group consisting of Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII. In yet other embodiments the first nicking enzyme and the second nicking enzyme comprise at least one enzyme combination from the group consisting of Nt.BbvcI/Nb.BbvcI respectively and Nb.BbvcI/Nt.BbvcI respectively.

In some embodiments, the base extension reaction of (b) comprises contacting the first DNA strand with a polymerase, one or more nucleotides, and a ligase.

The present invention also provides a method of generating a linked-paired-end nucleic acid fragment from a DNA sample. The method comprises contacting a double-stranded DNA template having a first and a second DNA strand with a restriction endonuclease to form overhang double stranded cuts of the DNA at a sequence-specific location, and conducting a base extension reaction on the fragments of the overhang DNA thereby generating blunt end double-stranded DNA fragments that shares common linker sequences between each other.

In some embodiments, the nicking endonuclease is type II endonuclease. In some embodiments, the type II endonuclease is from subtype IIb. In other embodiments, the endonuclease comprises one or more endonucleases selected from the group consisting of BcgI, Bsp24I, BaeI, CjeI, and CjePI. In yet other embodiments, the endonuclease enzyme is BaeI.

In some embodiments, base extension reaction comprises contacting the first DNA strand with a polymerase, one or more nucleotides, and a ligase.

In some embodiments, the generated fragments are 50 kb or less and the adjacent linker fragments share at least one selected from the group consisting of 100 bp or more and 50 bp or more.

In some embodiments, the linked-paired-end fragments are sequenced with at least one high throughput next generation sequencing platform selected from the group consisting of Illumina sequencing, SOLiD sequencing, 454 pyrosequencing and Ion Torrent semiconductor sequencing. In other embodiments, the library preparation for sequencing comprises circularizing the linked-paired-end fragments; fragmenting and size selecting the fragments of interest and ligating adaptors at a location selected from the group consisting of both ends of the fragments for paired-end sequencing and one end of the fragments for singled-end sequencing.

In yet another aspect, the present invention provides a method of whole genome mapping. The method comprises constructing a linked-paired-end sequencing library wherein the linked DNA fragments are used and mapping the sequence reads of the sequenced libraries to the reference genome map.

In some embodiments, the genome mapping comprises a haplotype sequence assembly. In other embodiments, the haplotype comprises the human major histocompatibility (MHC) region.

In a further aspect, the present invention provides method of analyzing computationally the nucleotides sequences from linked-paired-end sequenced fragments. The method comprises performing a pairwise comparison of all overlap nucleotides sequence read, and correlating the nucleotides sequence read to a sequence assembly, a genetic or cytogenetic map, a structural pattern, a structural variation, physiological characteristic, a methylation pattern, an epigenomic pattern, a location of a CpG island, a single nucleotide polymorphism (SNP), a copy number variation (CNV), or a combination thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

As seen in FIG. 2, random hexamers are used as a common technique when synthesizing cDNA. Other options include ssDNA ligation to a hairpin oligonucleotide and adding a mononucleotide run such as polyA to the ssDNA with terminal transferase followed by annealing of a complementary oligonucleotide such as polyT.

Figure 6:
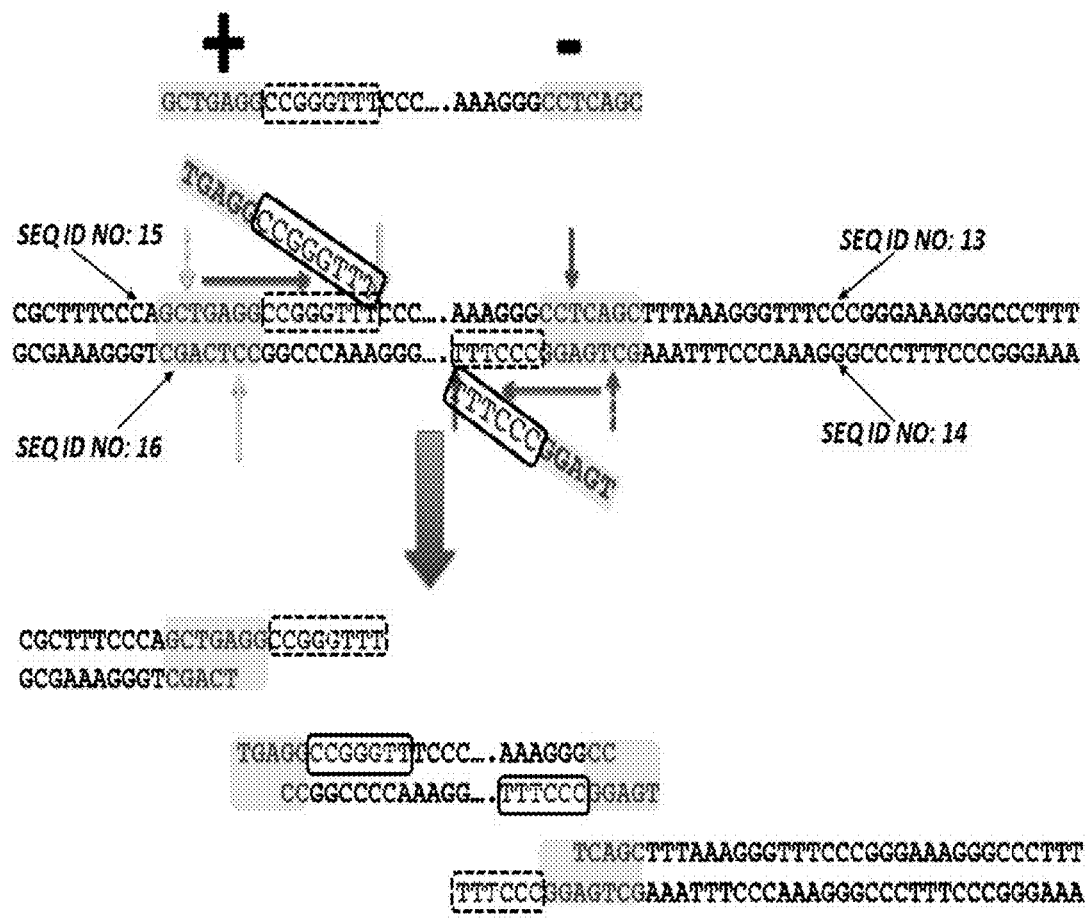

FIG. 6 is a schematic showing how the nickase recognition site orientation results in a fragment that has no long 3' overhangs. It is called "+−" because the upstream recognition site is nicked on the top strand and the downstream recognition site is nicked on the bottom strand during the first round of nicking (SEQ ID NOs: 13-16).

Figure 7:
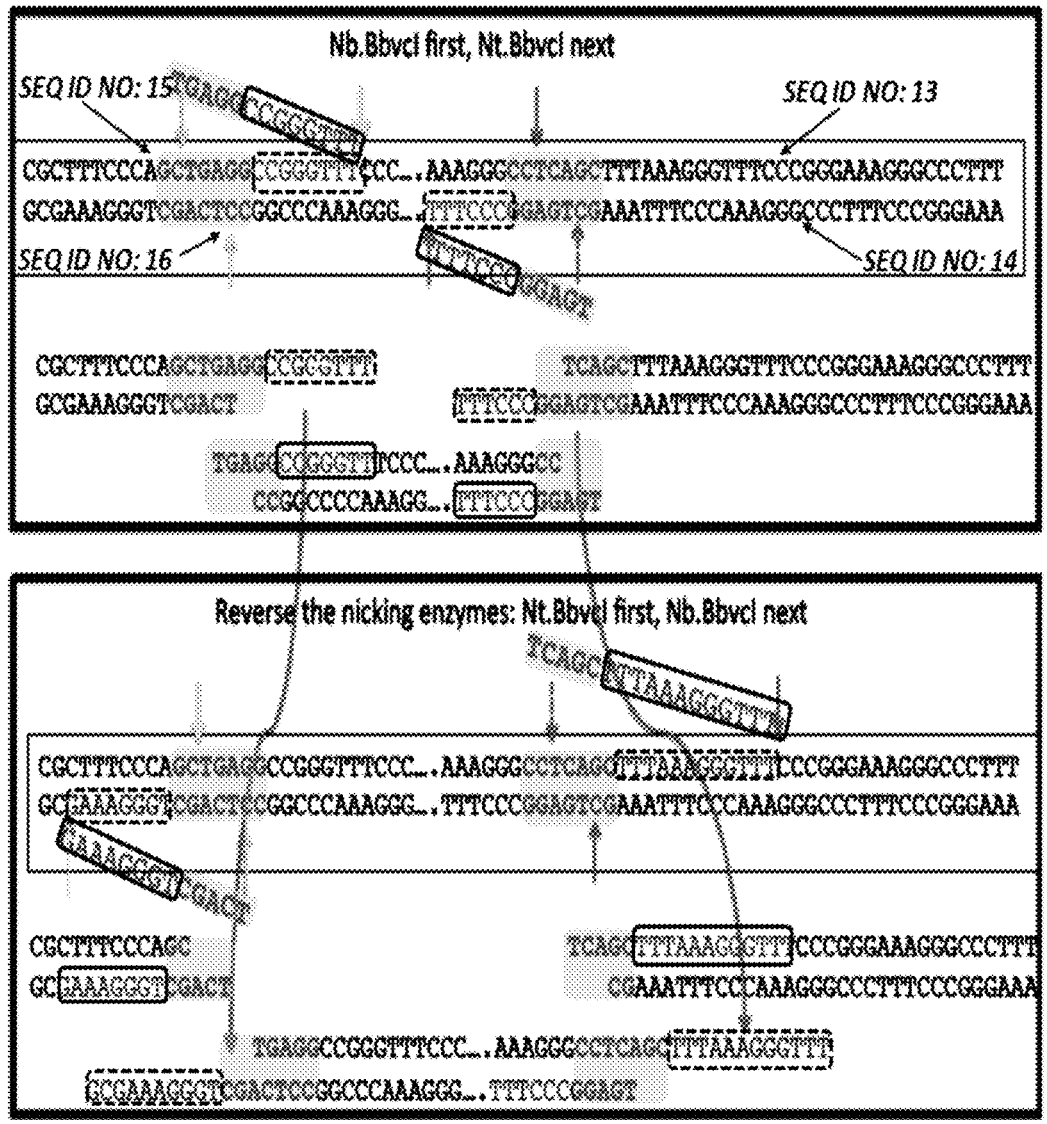

FIG. 7 is a schematic illustrating that a switch in the order in which the nickases are used results in a change in the fragment types generated. Here, a "+−" fragment is generated when Nb.BbvCI is used first, followed by Nt.BbvCI. By reversing the order and using Nt.BbvCI first followed by Nb.BbvCI, that same fragment is "−+" instead. Generation of identical libraries can be thus initiated, differing only in the order of nickases used, and then the libraries are pooled together after the second nicking step resulting in a more robust library. This mitigates the possibility that certain fragment types might be underrepresented in the final sequencing reaction (SEQ ID NOs: 13-16).

Figures 8A, 8B, 8C, 8D:
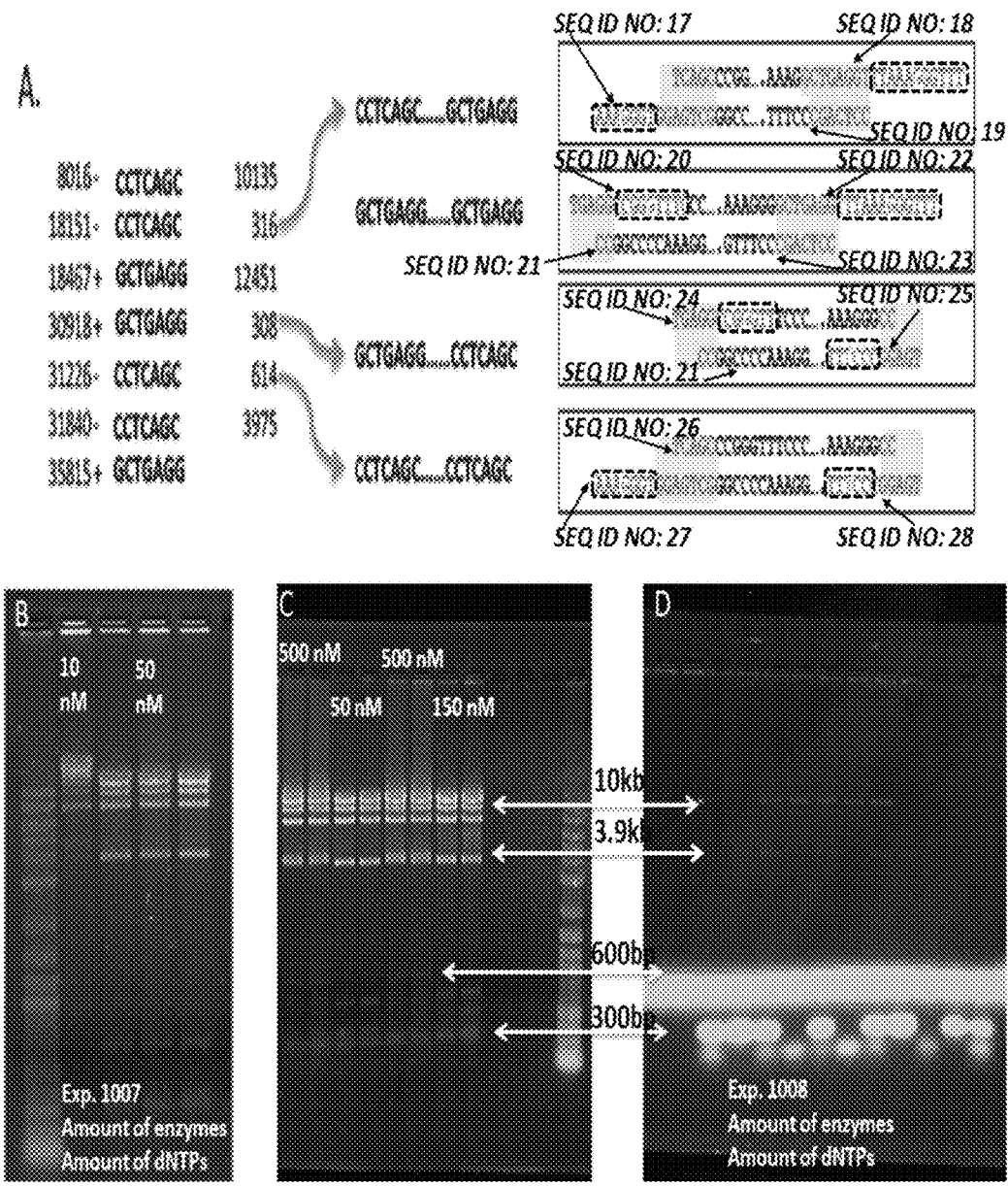

FIGS. 8A-8D are series of schematics and images exemplifying the implementation of Nick-Flap-Nick scheme on Lambda phage genome. FIG. 8A: Column 1 shows the location of nickase recognition sites in the Lambda phage genome. Column 2 indicates the sequence of the recognition site on the top strand. Column 3 describes the size in base pairs of the fragment generated downstream of that nicking site. Column 4 shows the sequence of the recognition site on the top strand on either end of four different fragments. Column 5 shows the fragment type created by the different nicking site orientations in those four Lambda phage genome fragments (SEQ ID NOs: 17-28). FIG. 8B: Flap length is determined by nucleotide concentration during the Flap step. Nucleotide concentrations that are too low result in very short flaps that reduce the efficiency of the second nickase. As a result, adjacent fragments do not melt apart and a partial digest pattern is seen. FIG. 8C: Variable mobility is seen among the lower molecular weight fragments as differing amounts of nucleotides are used in the flap step to create flaps of different lengths. FIG. 8D: Two Cy3 conjugated oligonucleotide probes complementary for two specific 3' overhangs near BbvCI sites in the Lambda phage genome were hybridized to samples after the Nick-Flap-Nick scheme. They were detected in this fluorescence image (same gel as FIG. 8C) having the expected mobility in samples with sufficiently high nucleotide concentrations during the flap step, indicating that the 3' overhangs are generated as disclosed herein. Long strip of fluorescence is bromophenol blue, smaller blobs of fluorescence at the bottom are free probes.

Figures 9A, 9B, 9C:
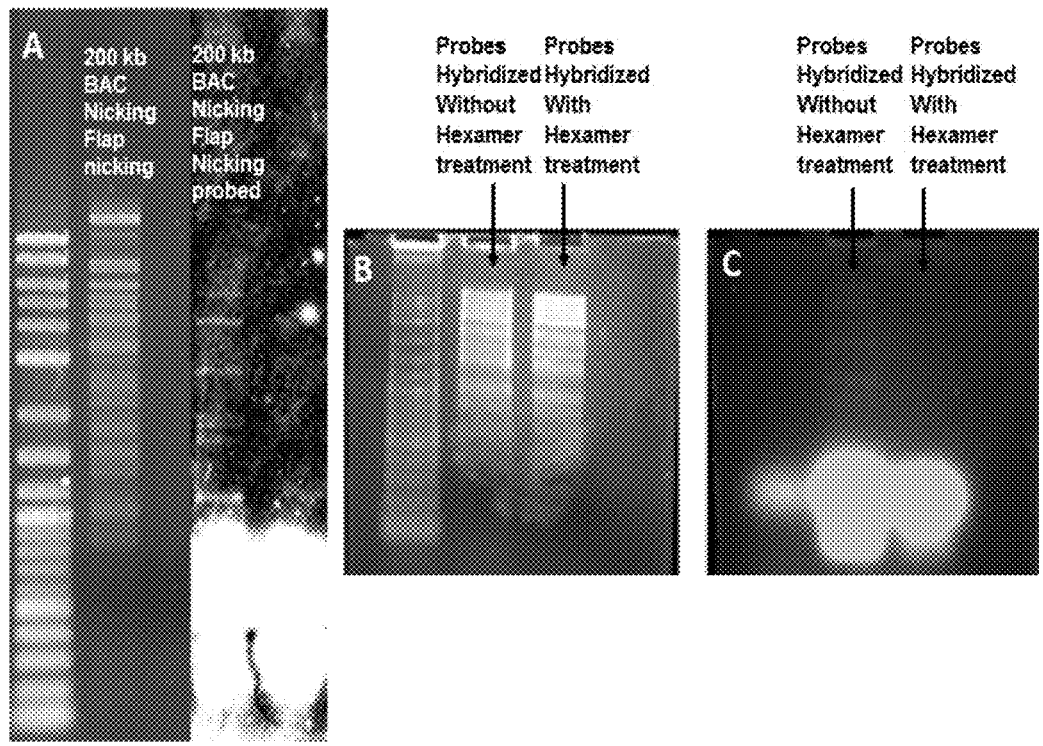

FIGS. 9A-9C are series of gel images illustrating the linker sequences generated on a 200 kb BAC with human genomic DNA insert using the Nick-Flap-Nick scheme. FIG. 9A: Lane 1: 2-log ladder, lane 2: BAC after Nick-Flap-Nick and hybridized with a Cy3 conjugated oligonucleotide probe complementary to a common repetitive sequence that contains a BbvCI site. Second image shows the same gel, fluorescence image with ladder cropped out. FIG. 9B: Restoring the 3' overhangs to dsDNA abolishes probe hybridization. Lane 1: 2-Log Ladder. Lane 2: The same BAC as FIG. 9A, after Nick-Flap-Nick scheme, and hybridized with the same fluorescent probe. Lane 3: Same as Lane 1 but after Nick-Flap-Nick scheme, long 3' overhangs were converted to dsDNA using the random hexamers method. FIG. 9C: Fluorescence image of the same gel as panel FIG. 9B. Probe hybridization is abolished by restoration of dsDNA by random hexamer method.

FIG. 10 is a schematic displaying another scheme of the present invention called the "Nick-Flap-T7 Endonuclease" scheme for creating linker sequence (SEQ ID NOs: 5-6). The first two steps are identical to the Nick-Flap-Nick scheme, but instead of nicking the second strand at the nickase recognition site, T7 Endonuclease is used to nick the second strand at the flap. This generates a 5' overhang, rather than a 3' overhang. Conversion of the overhang to dsDNA is as simple as extending the 3' recessed end with a DNA polymerase.

Figure 3:
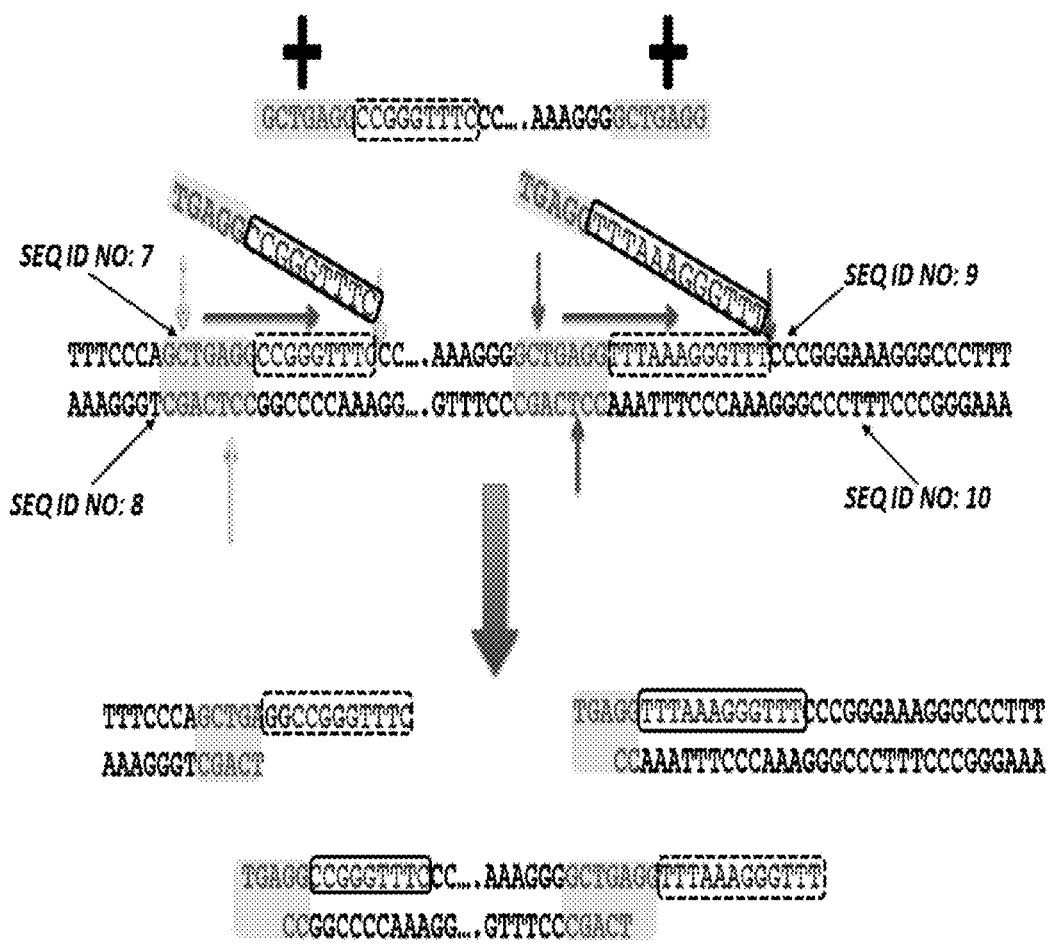
FIG. 3 is a schematic depicting the four types of fragments created in the Nick-Flap-Nick scheme (SEQ ID NOs: 7-10). These are described herein based upon which strand is cut first on either end of the fragment. Shown here, the two adjacent nickase recognition sites (in grey shaded area) are oriented such that they are both nicked on the top (+) strand first. This recognition site orientation gives rise to a fragment with the long 3' overhang on the downstream end. This is called a "++" fragment.
Figure 4:
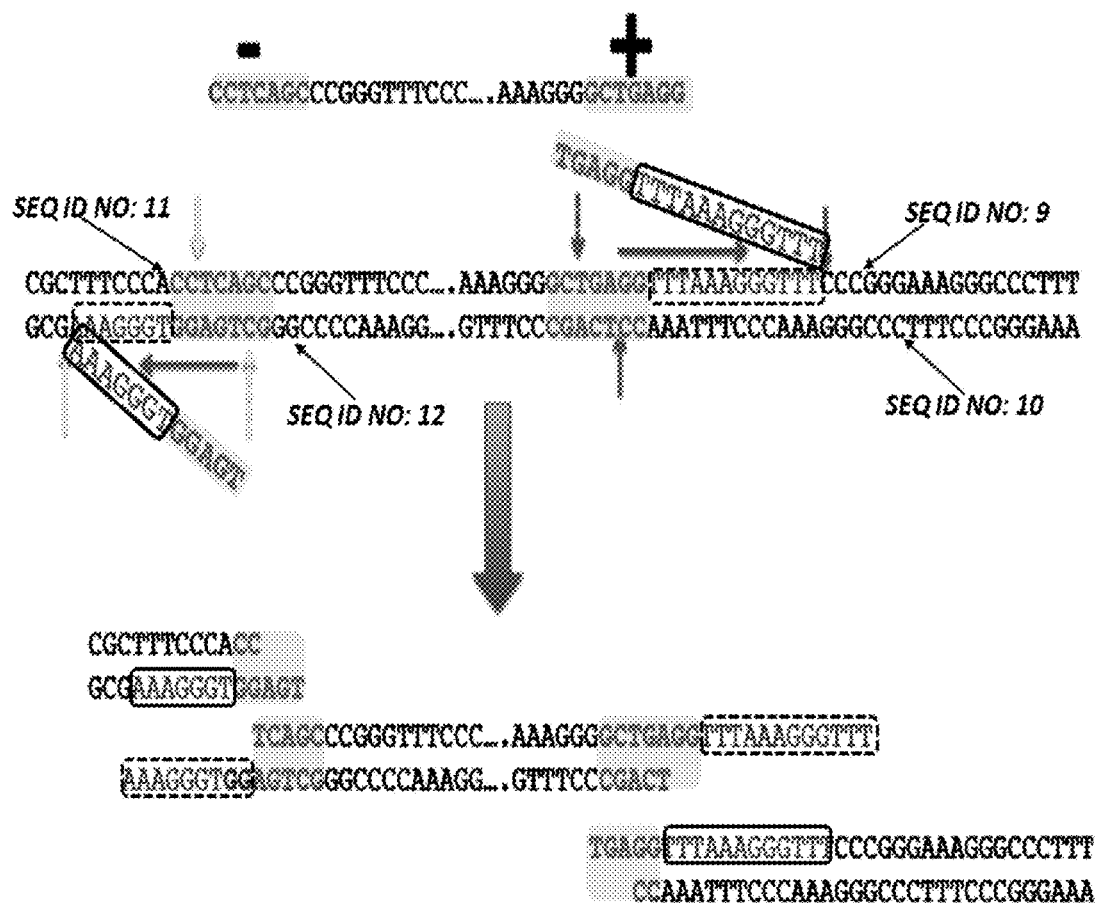
FIG. 4 a schematic showing how the nickase recognition site orientation results in a fragment that has a long 3' overhang on both ends. It is called "−+" because the upstream recognition site is nicked on the bottom strand and the downstream recognition site is nicked on the top strand during the first round of nicking (SEQ ID NOs: 9-12).
Figure 5:
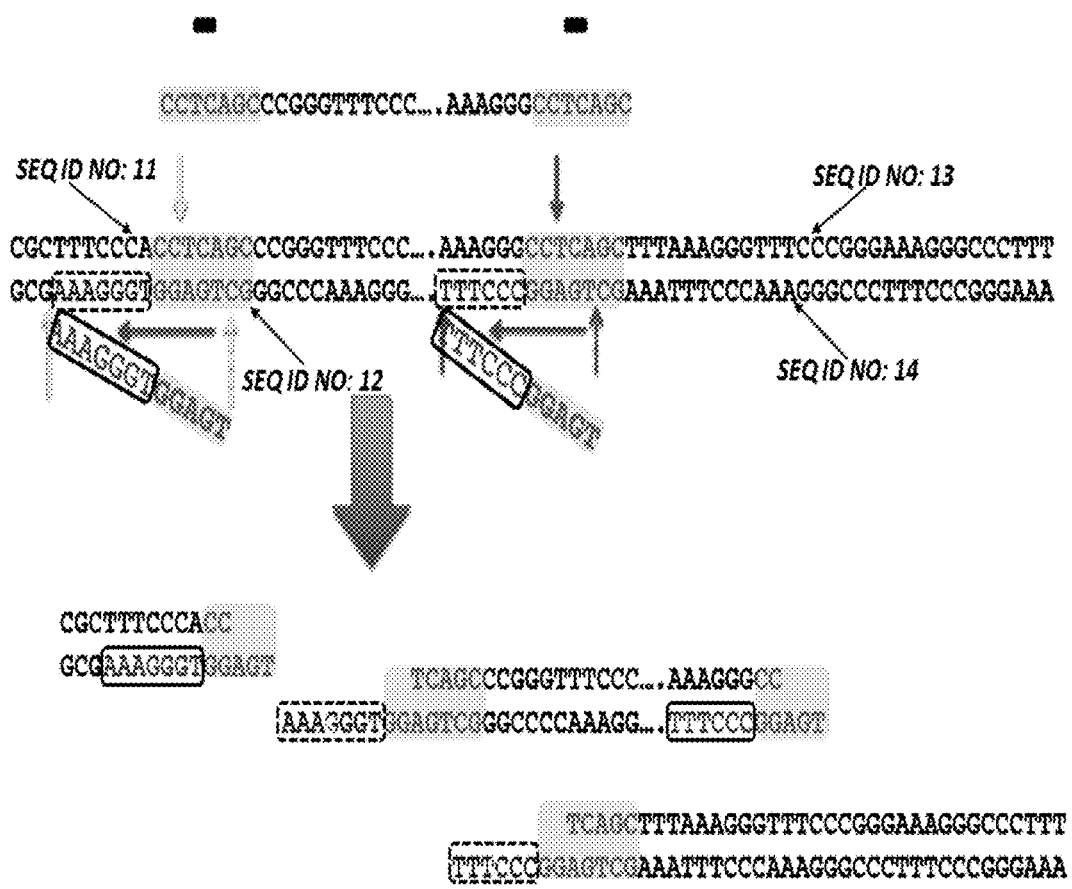
FIG. 5 is a schematic showing how the nickase recognition site orientation results in a fragment that has a long 3' overhang on the upstream end. It is called "−−" because both recognition sites are nicked on the bottom strand during the first round of nicking (SEQ ID NOs: 11-14).
Figure 11:
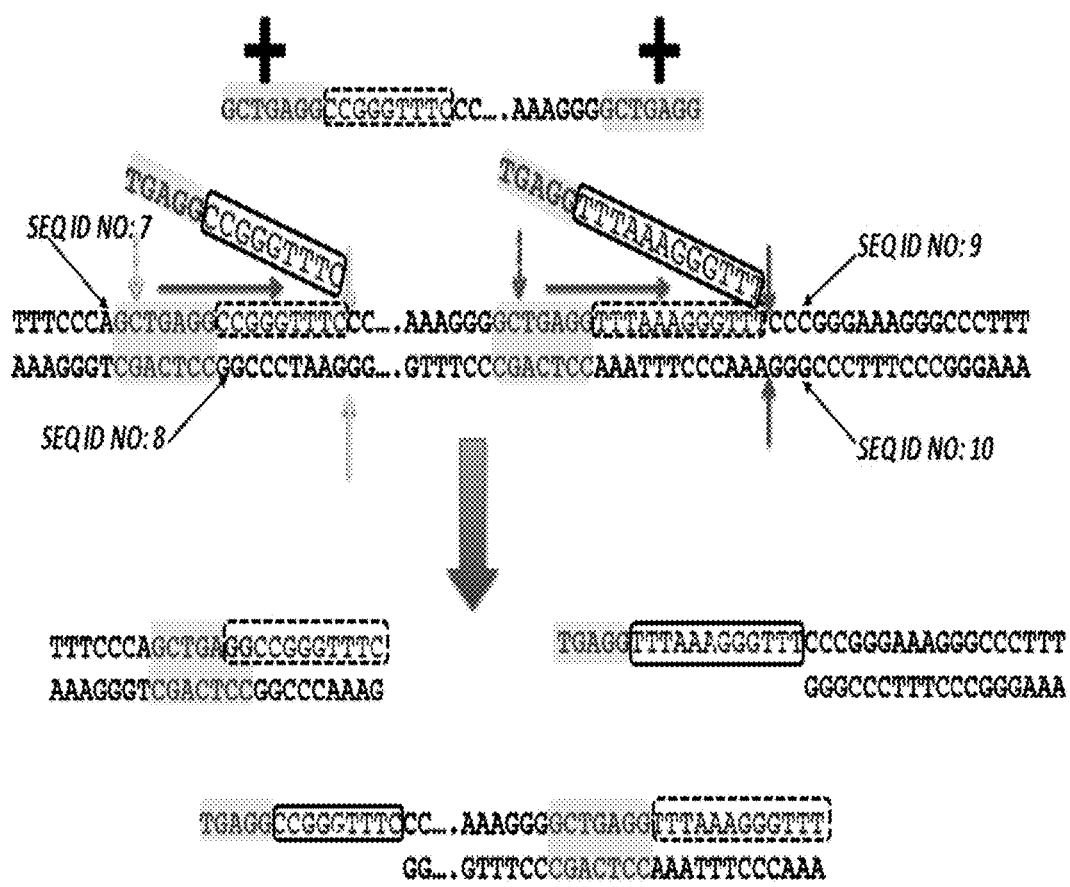

FIG. 11 is a schematic showing that as T7 Endonuclease nicks the second strand close to the break in the first strand, the flap becomes the overhang (SEQ ID NOs: 7-10). Another consequence of this difference between "Nick-Flap-T7 Endonuclease" scheme and the "Nick-Flap-Nick" scheme is that the single stranded sequences generated by adjacent nickase recognition sequences of a given orientation are on different fragments between the two schemes (see FIG. 3). Here, the two adjacent nickase recognition sites are oriented such that they are both nicked on the top (+) strand first. This recognition site orientation gives rise to a "++" fragment with the long 3' overhang on the upstream end.

Figure 12:
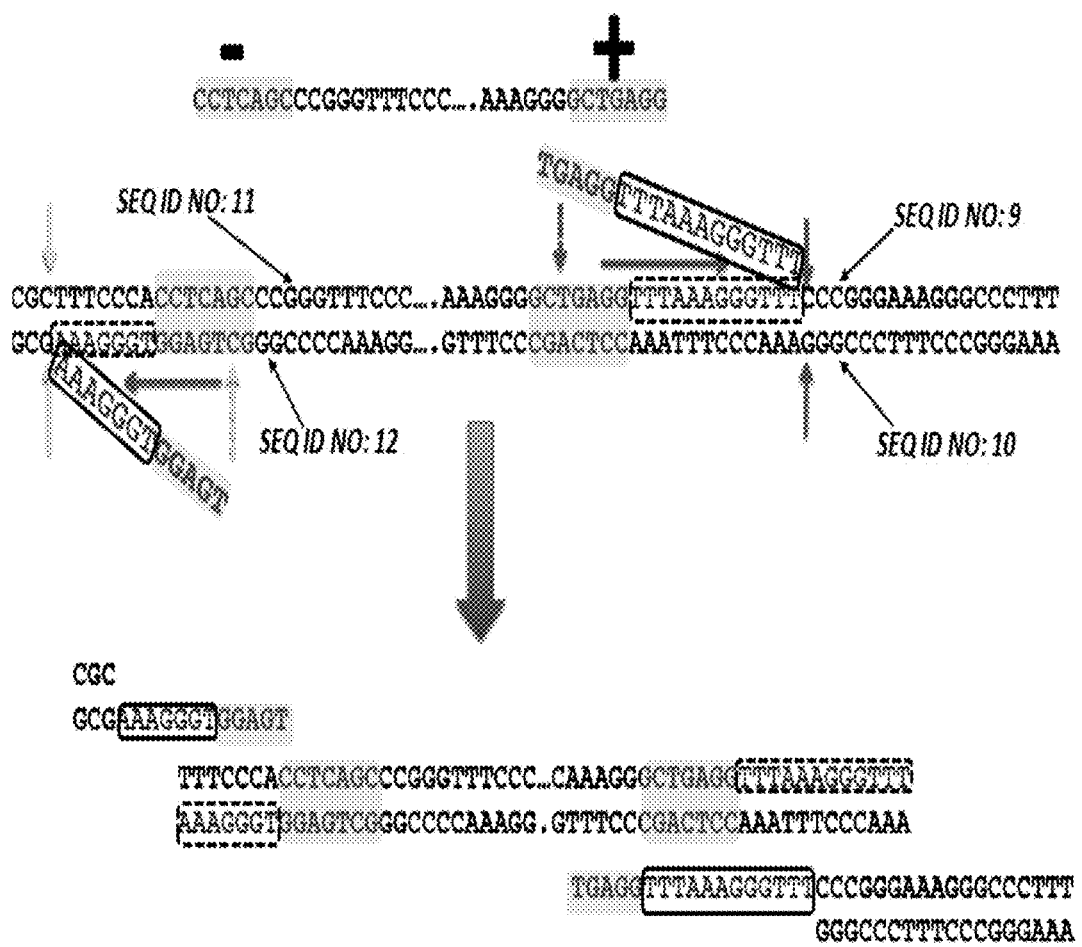

FIG. 12 is a schematic showing that the nickase recognition site orientation results in a fragment that has no long 3' overhangs. It is called "−+" because the upstream recognition site is nicked on the bottom strand and the downstream recognition site is nicked on the top strand during the first round of nicking (SEQ ID NOs: 9-12).

Figure 13:
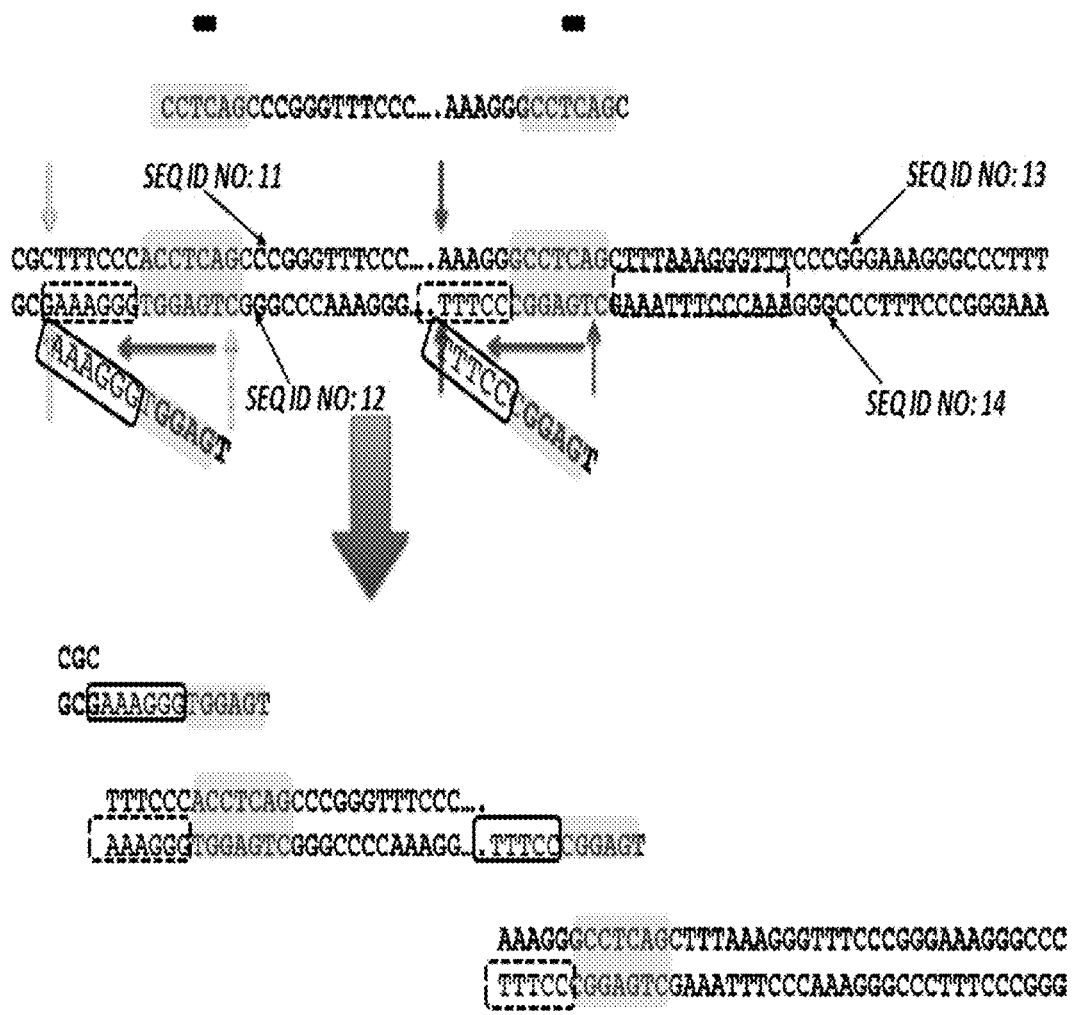

FIG. 13 is a schematic showing that the nickase recognition site orientation results in a fragment that has a long 3' overhang on the downstream end. It is called "−−" because both recognition sites are nicked on the bottom strand during the first round of nicking (SEQ ID NOs: 11-14).

Figure 14:
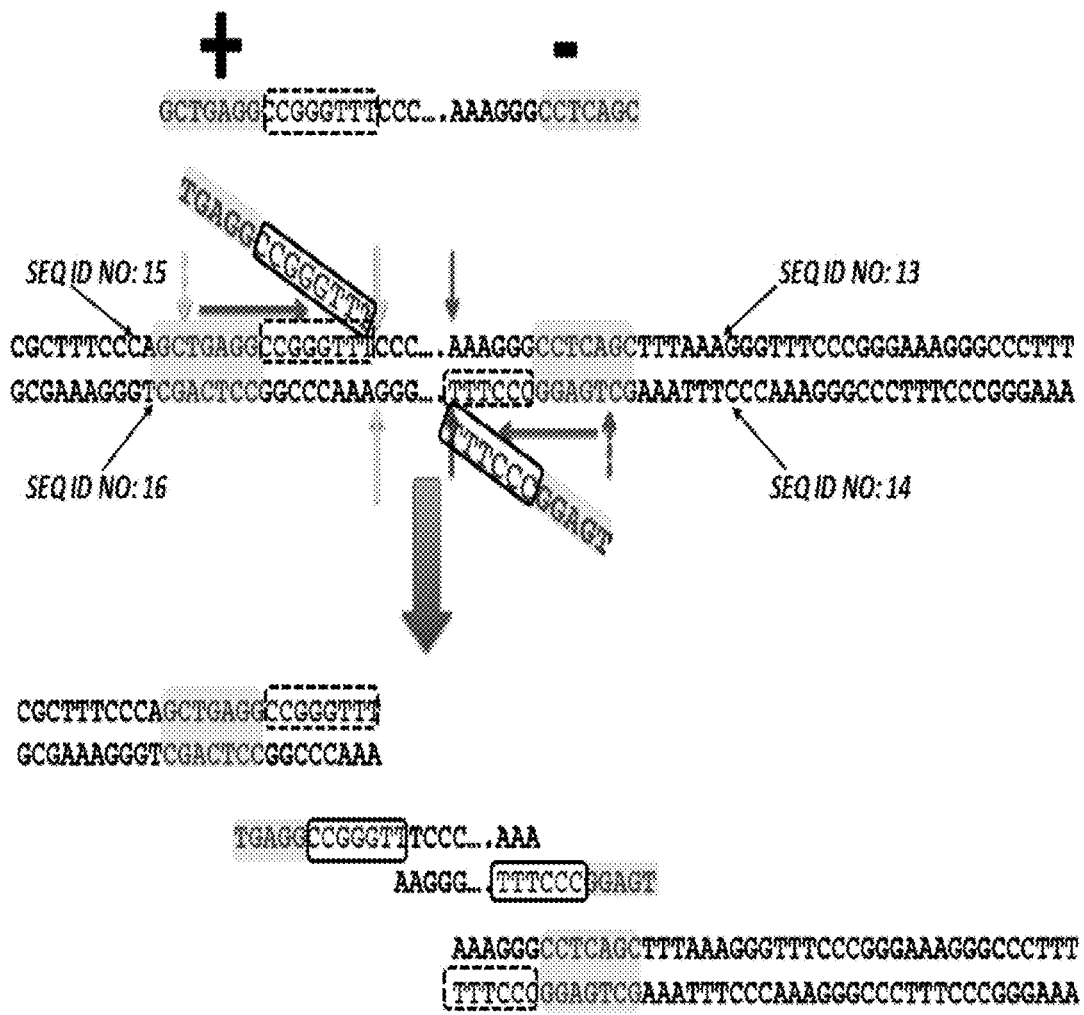

FIG. 14 is a schematic showing that the nickase recognition site orientation results in a fragment that has a long 3' overhang on both ends. It is called "−+" because the upstream recognition site is nicked on the bottom strand and the downstream recognition site is nicked on the top strand during the first round of nicking (SEQ ID NOs: 13-16).

Figures 15A, 15B, 15C:
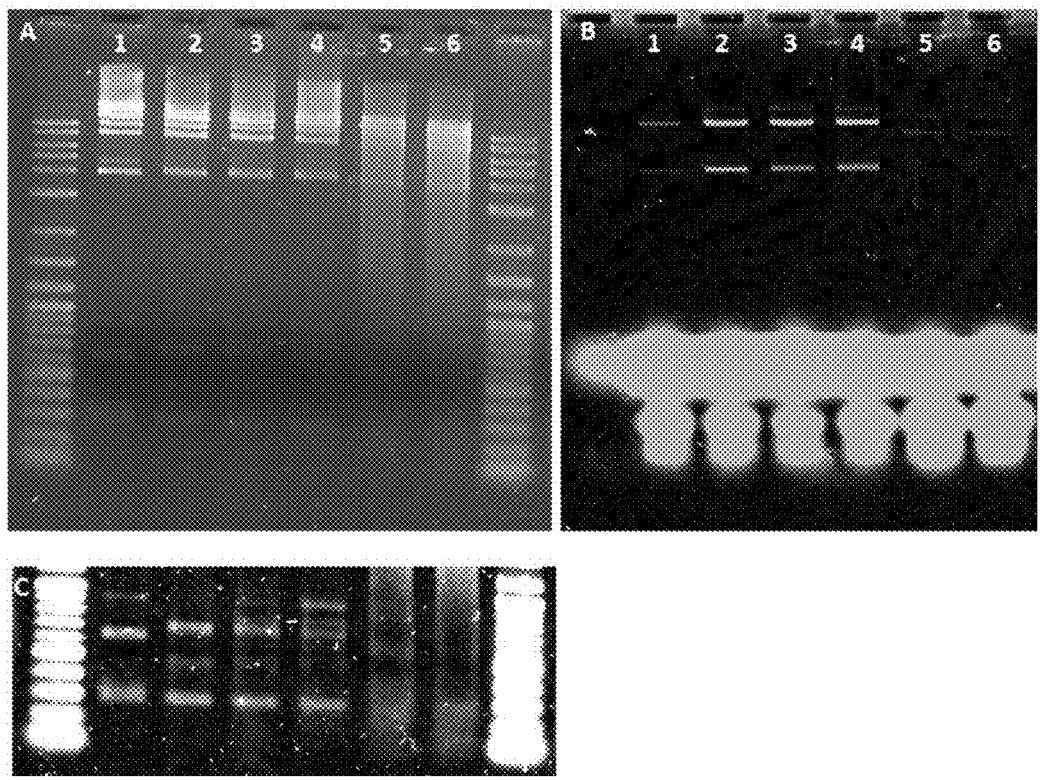

FIGS. 15A-15C are series of gel images depicting the implementation of Nick-Flap-T7 Endonuclease scheme on Lambda phage genome. FIG. 15A: Sybr green stained gel. Lanes 1 and 4: Lambda DNA, treated with nick-flap-nick scheme, matches well with the predicted fragments size. Lane 5-6: Lambda DNA, treated with nick-flap-T7 endonuclease, matches well with predicted fragment size. FIG. 15B: Fluorescent gel. Fluorescent probes are hybridized to specific flap single stranded flap sequences. In lanes 1 and 4, probes are hybridized to 8 kb and 4 kb fragments, while the same probes are hybridized to 10 kb and 12 kb fragments in nick-flap-T7 endonulcease scheme. FIG. 15C. A high contrast view of short fragments in Sybr stained gel of FIG. 15A.

Figure 16:
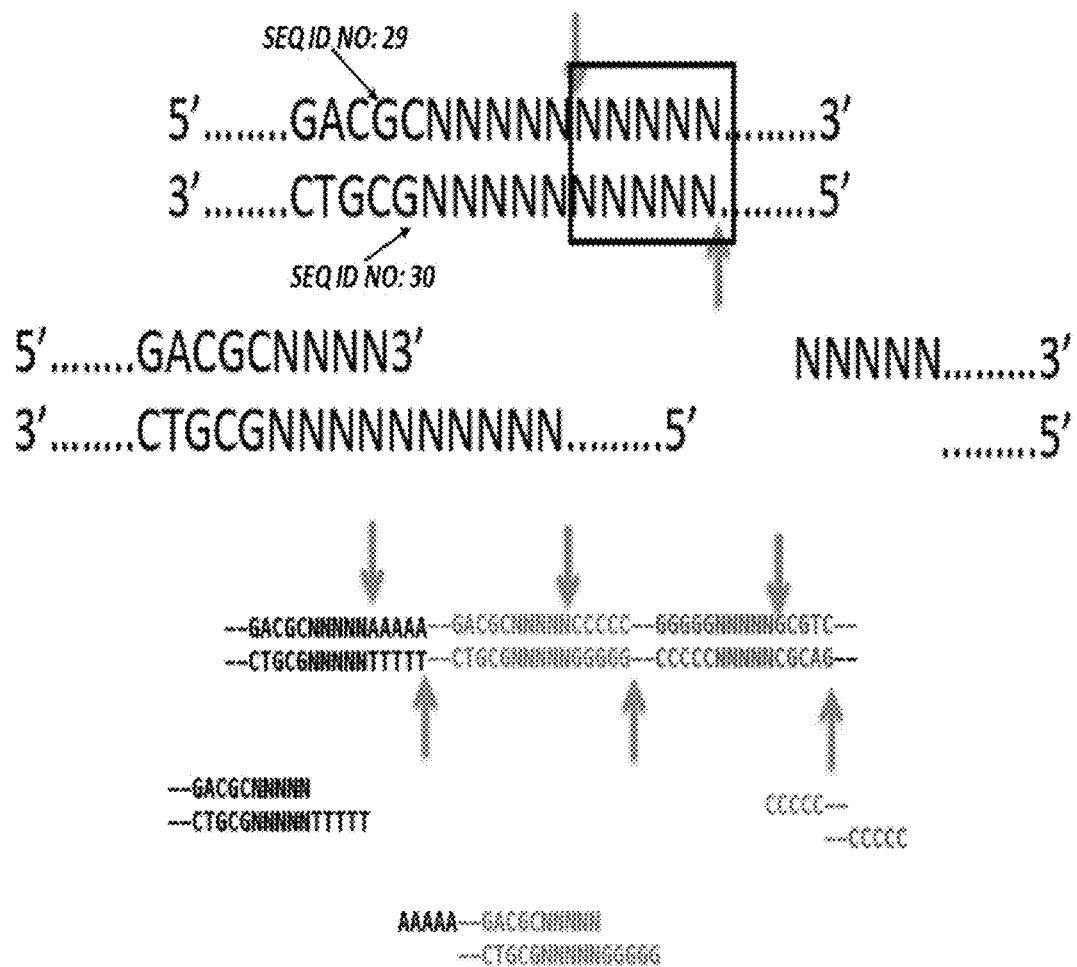

FIG. 16 is a schematic illustrating another method for generating linker sequences using restriction enzymes. In this scheme, enzymes are used that cut outside of the recognition site and sever each strand several nucleotides apart, preferably leaving 5' overhangs (SEQ ID NOs: 29-30). The overhangs are then filled in using a DNA polymerase.

Figure 17:
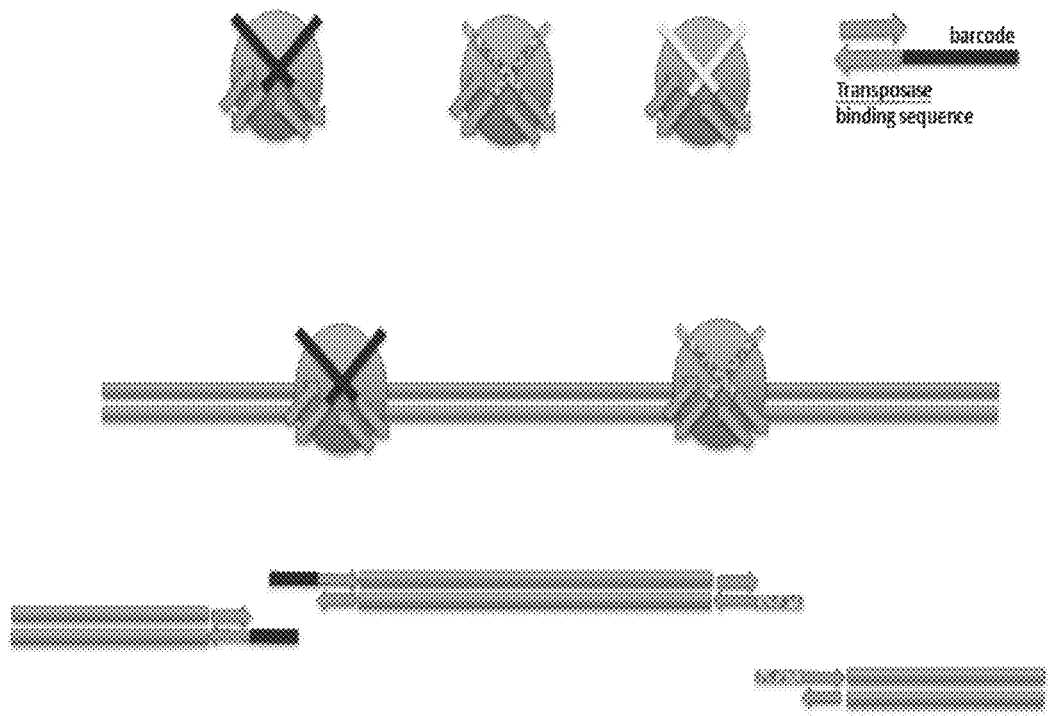

FIG. 17 is a representation demonstrating an in vitro transposition based scheme. Transposases catalyze the random insertion of excised transposons into DNA targets with high efficiency. In the present series of experiments, a transposon library was generated, such that each transposase binds to a unique oligo sequence. When inserted into DNA templates, the ends share the same sequences only at that specific locus.

Figure 18:
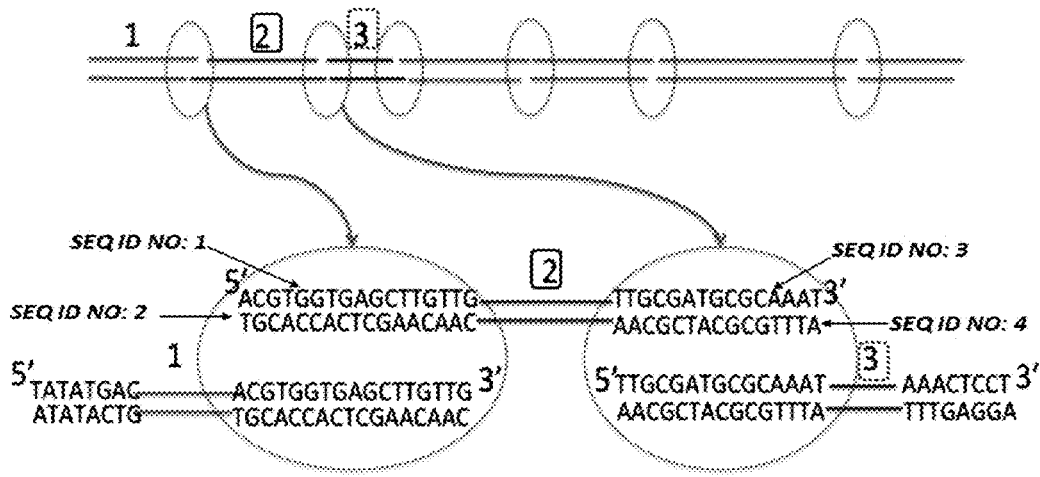

FIG. 18 is a schematic depicting the construction of de novo genome map with linked DNA fragments. The first step in this method is to break the DNA and generate the linker sequences at the ends. This can then be fed into conventional workflows for shotgun sequencing (SEQ ID NOs: 1-4).

Figure 19:
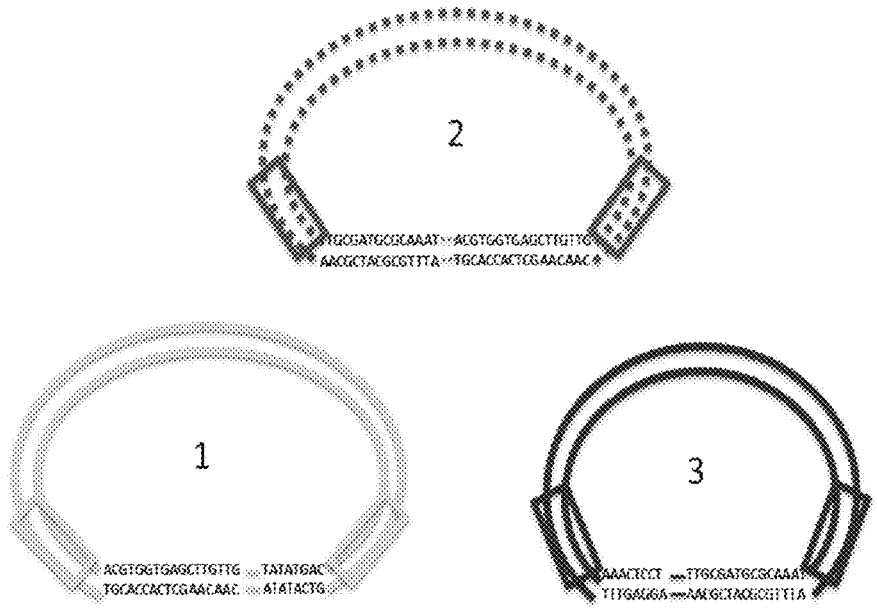

FIG. 19 is a schematic illustrating the construction of paired-end library by circularizing the fragments. In this next step, DNA fragments are generated with linker sequences and can be circularized to construct paired-end libraries. Size selection is optional.

Figure 20:
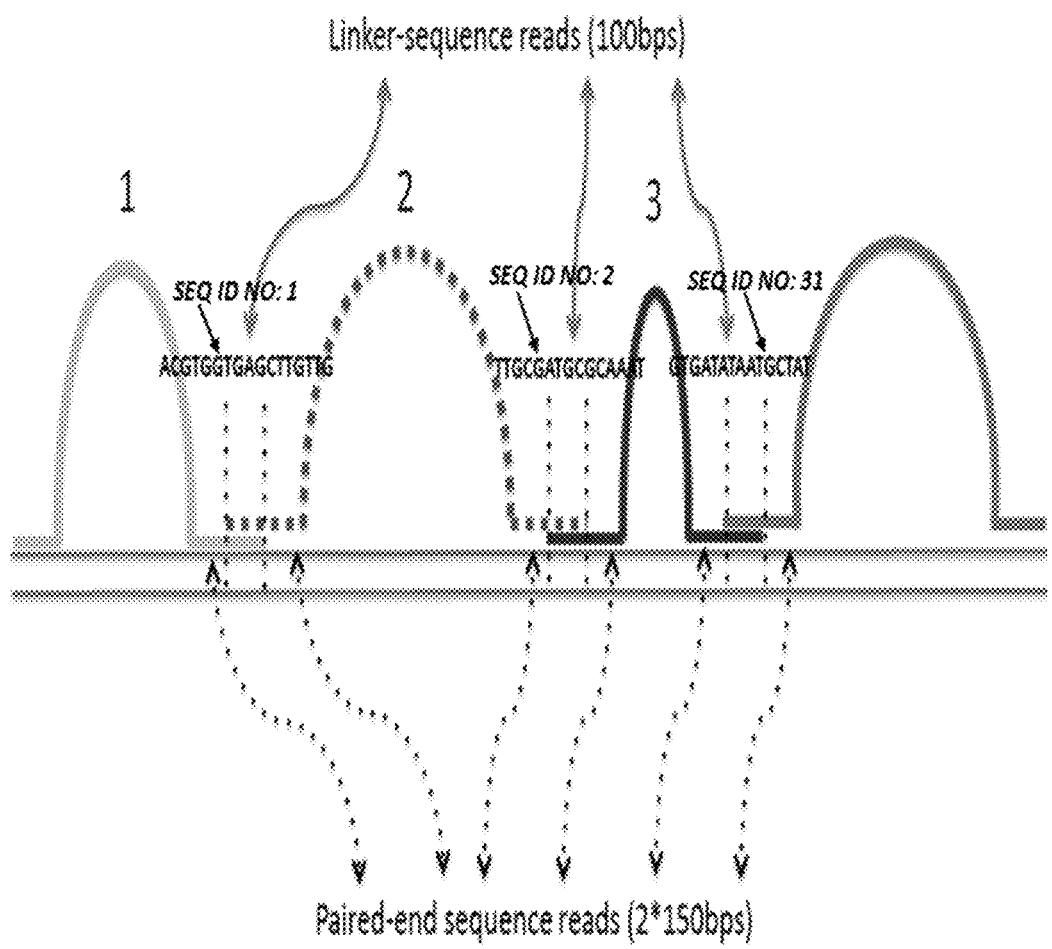

FIG. 20 is a schematic illustrating the sequenced fragments and the construction of the genome map (SEQ ID NOs: 1-2 and 31). This figure demonstrates that after sequencing, the paired-end libraries can be joined using the linker sequence reads. If size selected paired-end libraries are used, then the read spacing can contribute to an additional layer of detail to the scaffold. Polymorphisms in the linker-sequence reads enable separate scaffolds to be made for homologous chromosomes in diploid or polyploid genomes.

Figure 21:
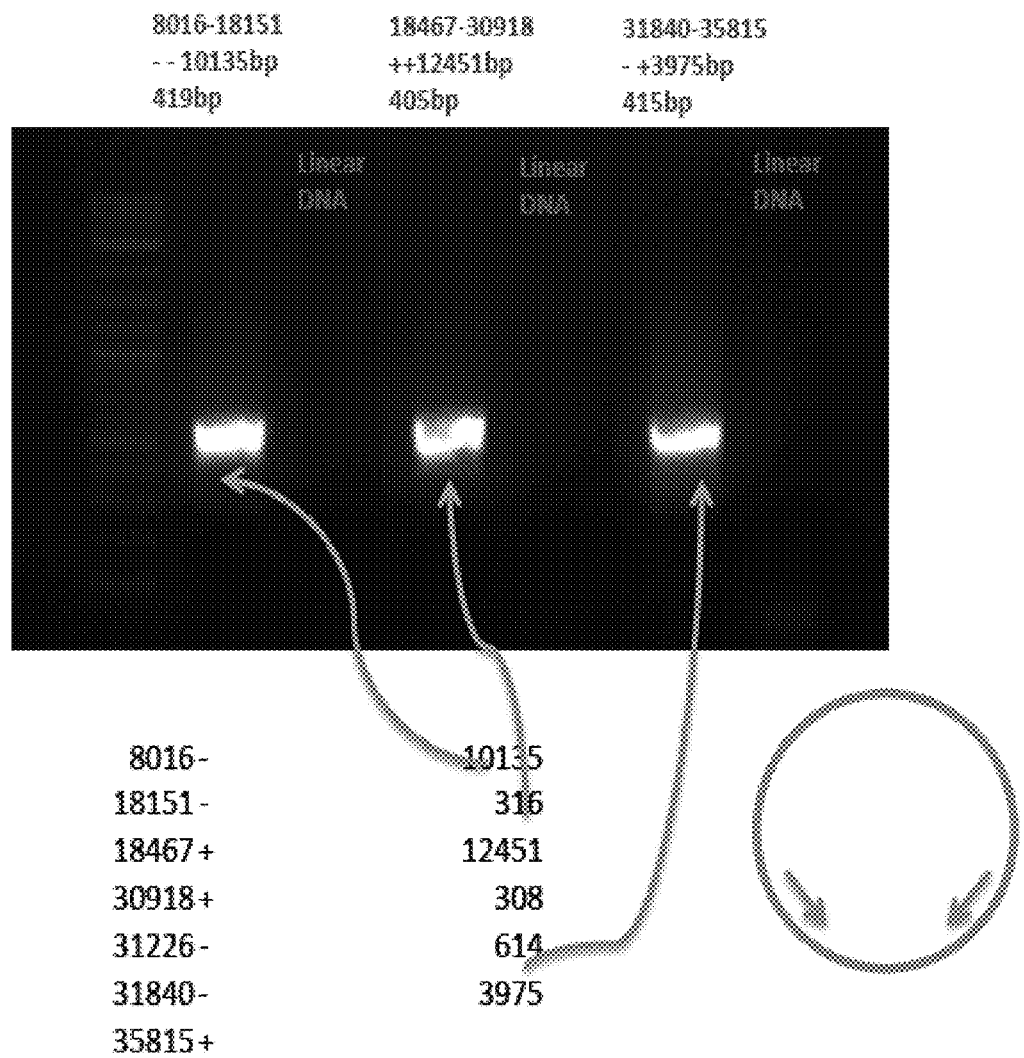

FIG. 21 is an image showing that a linked-paired-end library made of the Lambda phage genome has seven different circularized fragment loops. These loops were detected by PCR using primers that were designed to amplify the loops through the linker sequences, so that the priming sites were oriented away from each other with respect to the linear lambda genome. Lane 1: 2-log ladder. Lanes 2, 4 and 6: primers specific for the 10 kb, 316 bp, or 614 bp loops respectively, amplified the linked paired end library. Lanes three, five and seven: The same primers used in the lane to the left failed to amplify linear lambda genomic DNA.

Figure 22C:
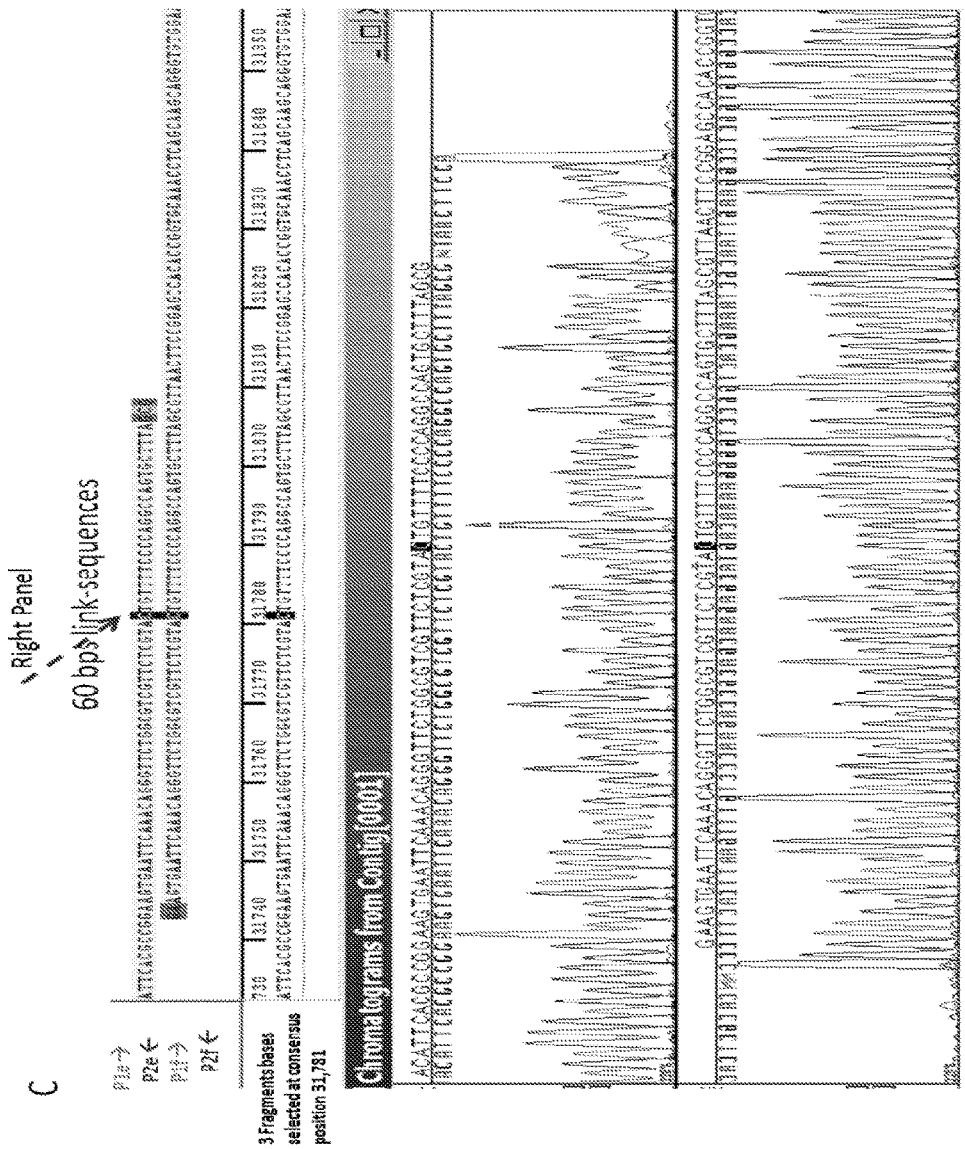

FIGS. 22A-22C are a series of representations schematizing the Lambda sequence map generated via linked-paired-end sequencing. The 48.5 kb lambda DNA molecules are broken at GCTGAGG Nb.BbvcI recognition motif and linker sequences are generated between the adjacent fragments FIG. 22A: sequence reads are aligned against Lambda sequences. FIG. 22B: The fragments are 8 kb, 10 kb, 0.3 bp, 12 kb, 0.6 bp, 0.3 bp, 4 kb, and 12 kb fragments. FIG. 22C: Two sequence reads of the linker sequences between 0.3 kb and 12 kb, 0.6 kb and 4 kb are shown.

Figure 23:
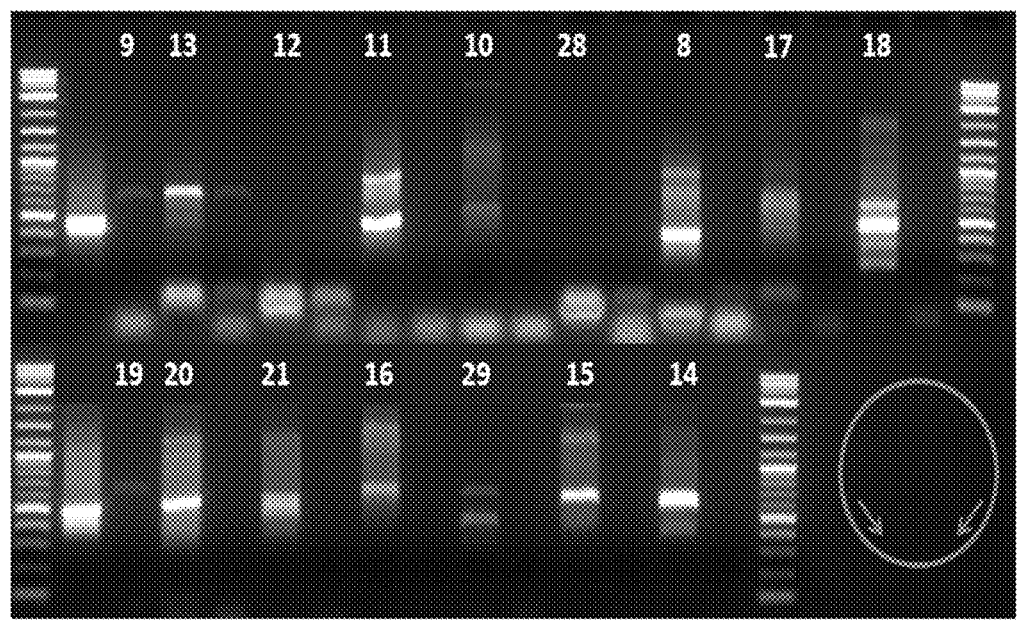

FIG. 23 is a gel image showing the circularization of the linked fragments from a 250 kb human back clone. PCR results confirm the presence of the linker sequences after circularization.

FIG. 24 is a table representing the summary of an in silico simulation on the human major histocompatibility complex (MHC). In the MHC region, linker sequences of 100 bp are sufficient to provide a high degree of uniqueness for joining sequencing reads.

Figure 25:
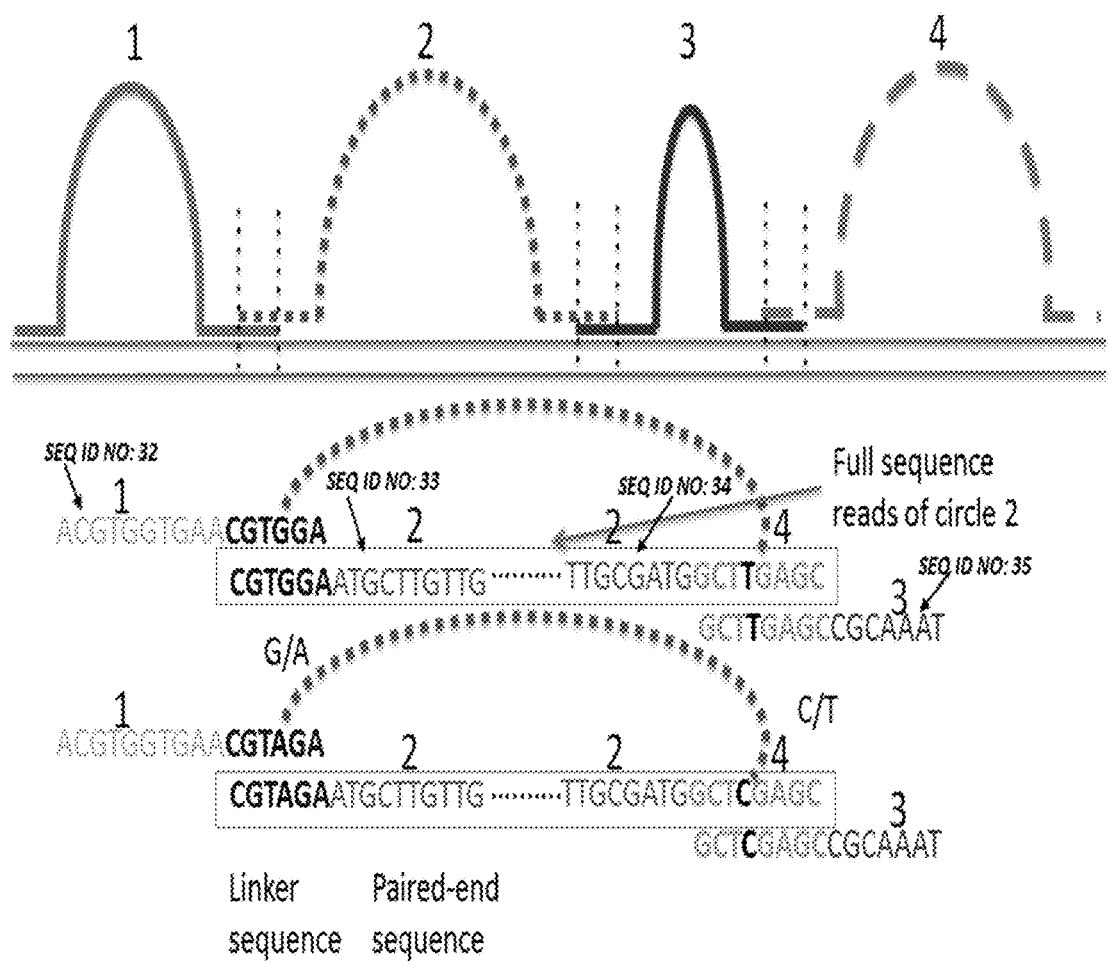

FIG. 25 is a schematic depicting how the linker sequence enables the generation of homolog-specific scaffolds and haplotyping at higher resolution than many currently available methodologies (SEQ ID NOs: 32-35).

FIG. 26 is a table summarizing the haplotype analysis of the human major histocompatibility complex region via in silico simulation. This simulation indicates that as little 4 haplotype blocks can cover 4.6 Mb of the human major histocompatibility complex (MHC) region.

Figure 27B:
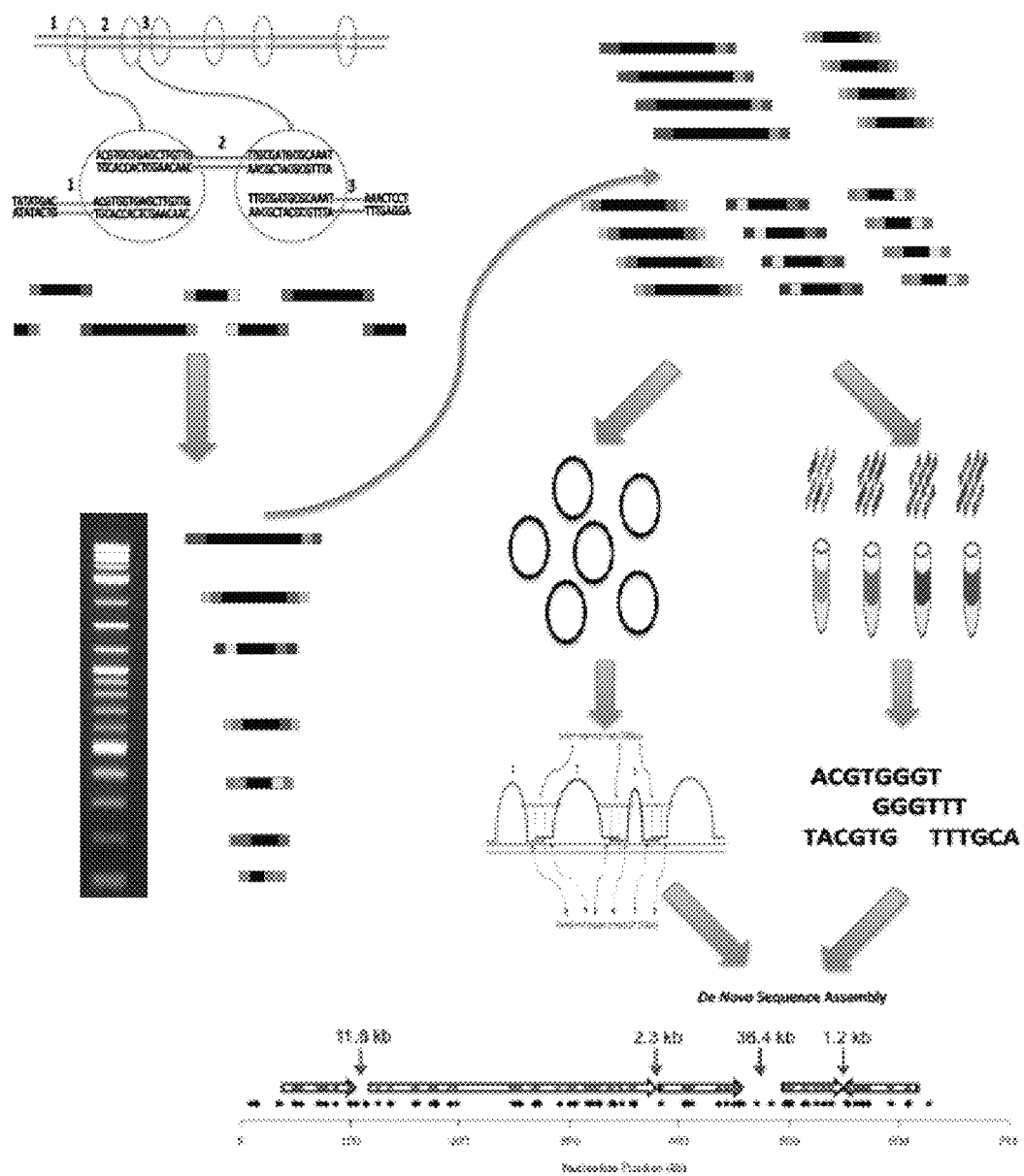

FIGS. 27A-27B are a series of representations reviewing the scheme of whole genome sequencing using linked DNA fragments. FIG. 27A depicts an example of an experimental workflow for whole genome mapping using the methods of the present invention Whole genome mapping is achieved as part of the invention. FIG. 27B illustrates a workflow scheme where the genomic DNA is fragmented and overlapping linker sequences are generated at the ends of the fragments. Some of the library is then used for traditional shotgun sequencing. The rest of the library is used for paired end sequencing. The fragments can be separated by molecular weight, as is typically done for conventional paired end sequencing, or they are left as pooled fragments. The fragments are circularized, similar to the conventional methodology, fragmented, and the circularization site is selected and sequenced from both ends. The linked-paired-end reads can be used to create a genome map, or a sequencing scaffold, to which the shotgun sequencing reads can be fit.

Figure 28:
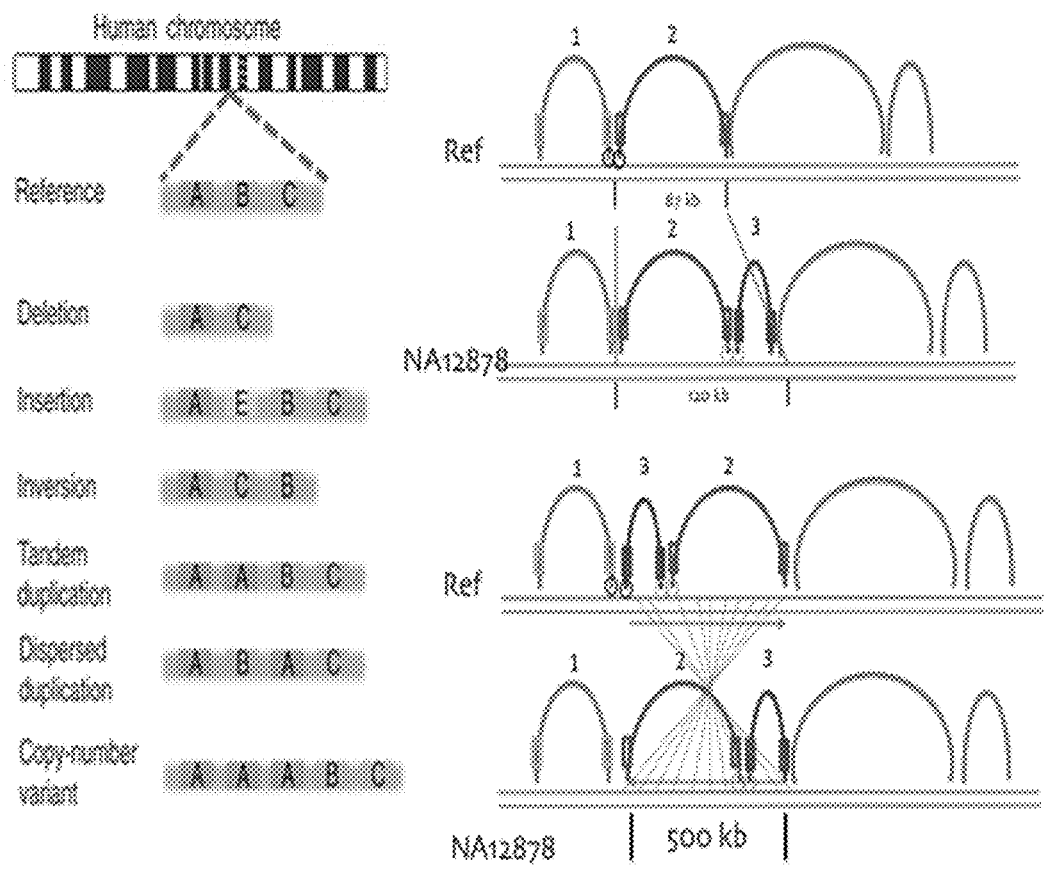

FIG. 28 is a schematic illustrating the structural variation analysis. Linked-paired-end sequencing can be used to detect structural variations that are impossible to resolve with conventional paired end sequencing. Because the paired end fragments are linked, large scale variants can be spanned by several fragments in a string. Shown are a 33 kb insertion and a 500 kb inversion.

Figures 29A, 29B:
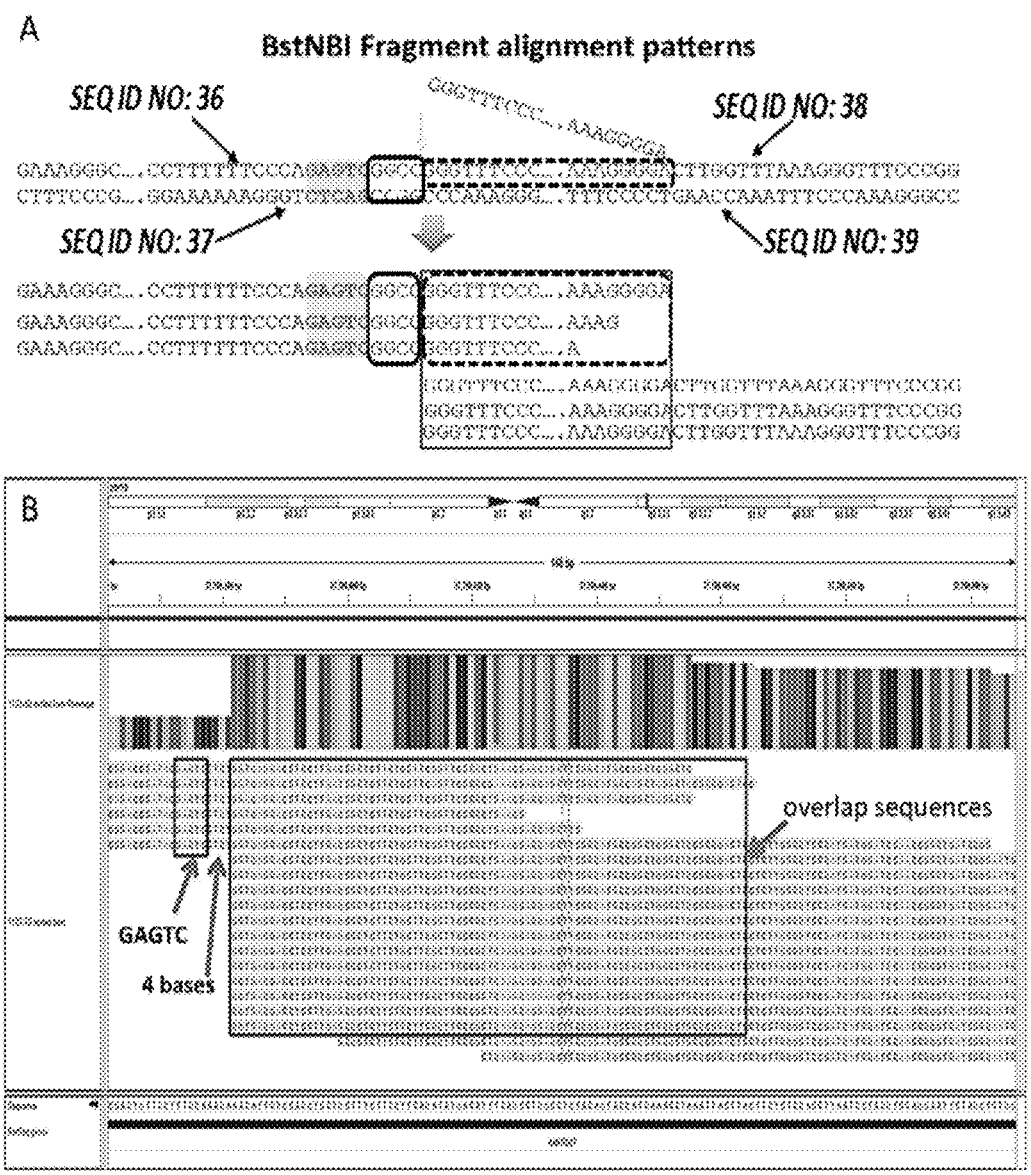

FIGS. 29A-29B are a series of schematics representing the sequence alignment structure of a haplotype scaffold (SEQ ID NOs: 36-39). FIG. 29A: Predicted sequencing read patterns with the nicking enzyme Nt. BStNBI. BstNBI nickase nicks four bases away from the BstNBI recognition motif (GAGTC). The DNA sequences shown in dotted lines are generated through polymerase extension, and may have various extension lengths. While the flap sequences, will all start four bases away from GAGTC. The predicted patterns are shown underneath of the arrow. FIG. 29B: Typical sequence alignments from Illumina MiSeq reads viewed in the Integrated Genome View (IGV). They fit the predicted patterns. These sequence alignment patterns are enriched and consistent through all nicking sites based on our sequencing results. The overlap sequences are the critical information and are subsequently used for the construction of the haplotype resolved scaffold.

Figure 30:
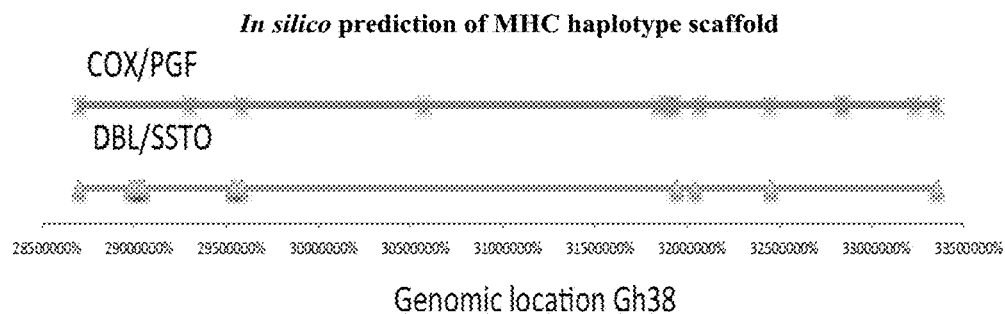

FIG. 30 is a schematic depicting the in silico prediction of MHC haplotype scaffold. Continuous haplotype blocks are shown as a straight line, and the breaks between haplotype blocks are shown as various symbols. For the DBL/SSTO sample, the longest continuous haplotype block is over 2.3 Mb, and the longest haplotype block is 1.1 Mb for the COX/PGF sample.

Figure 31:
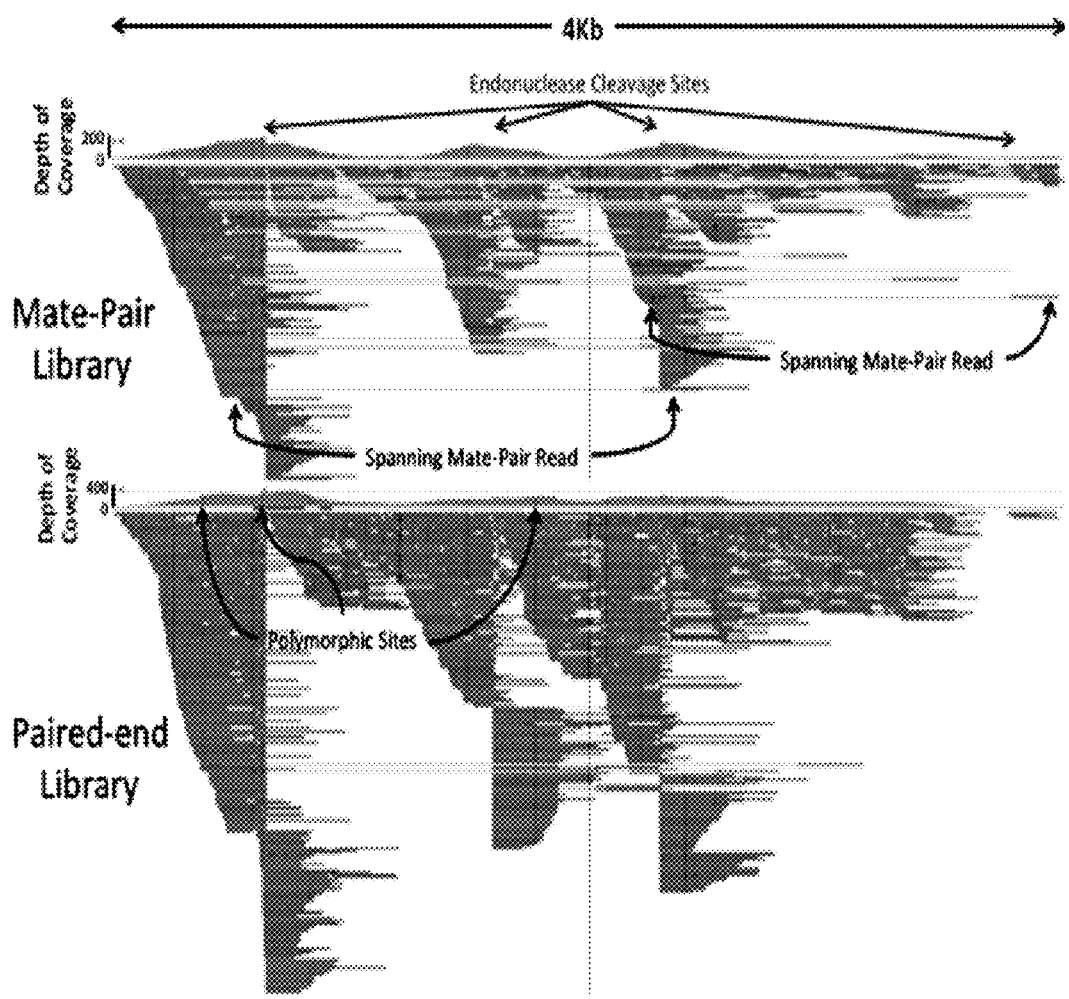

FIG. 31 is a schematic showing an example of haplotype block resolved by de novo MHC sequence assembly for a 4 kb region.

DETAILED DESCRIPTION OF THE INVENTION

The present invention relates to innovative means of DNA mapping and sequencing technology based on massively parallel sequencing with linked-paired-end sequencing libraries. Thus, in various embodiments described herein, the methods of the invention relate to methods of generating paired-end nucleic acid fragment sharing common linker nucleic acid sequences using a nicking endonuclease, a T7 endonuclease, a restriction enzyme or a transposase, methods of analyzing the nucleotides sequences from the linked-paired-end sequenced fragments and methods of de novo whole genome mapping.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

The term, "polynucleotide" includes cDNA, RNA, DNA/RNA hybrid, anti-sense RNA, siRNA, miRNA, snoRNA, genomic DNA, synthetic forms, and mixed polymers, both sense and antisense strands, and may be chemically or biochemically modified to contain non-natural or derivatized, synthetic, or semisynthetic nucleotide bases. Also, included within the scope of the invention are alterations of a wild type or synthetic gene, including but not limited to deletion, insertion, substitution of one or more nucleotides, or fusion to other polynucleotide sequences.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T".

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have a N-terminal and a C-terminal. The N-terminal will have an amino group, which may be free (i.e., as a NH2 group) or appropriately protected (for example, with a BOC or a Fmoc group). The C-terminal will have a carboxylic group, which may be free (i.e., as a COOH group) or appropriately protected (for example, as a benzyl or a methyl ester). A cyclic peptide does not have free N- or C-terminal, since they are covalently bonded through an amide bond to form the cyclic structure. Amino acids may be represented by their full names (for example, leucine), 3-letter abbreviations (for example, Leu) and 1-letter abbreviations (for example, L). The structure of amino acids and their abbreviations may be found in the chemical literature, such as in Stryer, "Biochemistry", 3rd Ed., W. H. Freeman and Co., New York, 1988. tLeu represents tert-leucine. neo-Trp represents 2-amino-3-(1H-indol-4-y)-propanoic acid. DAB is 2,4-diaminobutyric acid. Orn is ornithine. N-Me-Arg or N-methyl-Arg is 5-guanidino-2-(methylamino) pentanoic acid.

"Sample" or "biological sample" as used herein means a biological material from a subject, including but not limited to organ, tissue, cell, exosome, blood, plasma, saliva, urine and other body fluid, A sample can be any source of material obtained from a subject.

The terms "subject", "patient", "individual", and the like are used interchangeably herein, and refer to any animal, or cells thereof whether in vitro or in situ, amenable to the methods described herein. In certain non-limiting embodiments, the patient, subject or individual is a human. Non-human mammals include, for example, livestock and pets, such as ovine, bovine, porcine, canine, feline and murine mammals. Preferably, the subject is human. The term "subject" does not denote a particular age or sex.

The term "measuring" according to the present invention relates to determining the amount or concentration, preferably semi-quantitatively or quantitatively. Measuring can be done directly.

As used herein the term "amount" refers to the abundance or quantity of a constituent in a mixture.

The term "concentration" refers to the abundance of a constituent divided by the total volume of a mixture. The term concentration can be applied to any kind of chemical mixture, but most frequently it refers to solutes and solvents in solutions.

As used herein, the terms "reference", or "threshold" are used interchangeably, and refer to a value that is used as a constant and unchanging standard of comparison.

As used herein, "paired-end sequencing" is a sequencing method that is based on high throughput sequencing, particular based on the platforms currently sold by Illumina and Roche. Illumina has released a hardware module (the PE Module) which can be installed in an existing sequencer as an upgrade, which allows sequencing of both ends of the template, thereby generating paired end reads. Paired end sequencing may also be conducted using Solexa technology in the methods according to the current invention. Examples of paired end sequencing are described for instance in US20060292611 and in publications from Roche (454 sequencing).

As used herein the term "sequencing" refers to determining the order of nucleotides (base sequences) in a nucleic acid sample, e.g. DNA or RNA. Many techniques are available such as Sanger sequencing and high-throughput sequencing technologies (also known as next-generation sequencing technologies) such as the GS FLX platform offered by Roche Applied Science, based on pyrosequencing.

A "restriction endonuclease" or "restriction enzyme" refers to an enzyme that recognizes a specific nucleotide sequence (target site) in a double-stranded DNA molecule, and will cleave both strands of the DNA molecule at or near every target site, leaving a blunt or a staggered end.

A "Type-IIs" restriction endonuclease refers to an endonuclease that has a recognition sequence that is distant from the restriction site. In other words, Type IIs restriction endonucleases cleave outside of the recognition sequence to one side. Examples thereof are NmeAIII (GCCGAG(21/19)) and FokI, AlwI, Mme I. Also included in this definition are Type IIs enzymes that cut outside the recognition sequence at both sides.

A "Type IIb" restriction endonuclease cleaves DNA at both sides of the recognition sequence.

"Restriction fragments" or "DNA fragments" refer to DNA molecules produced by digestion of DNA with a restriction endonuclease are referred to as restriction fragments. Any given genome (or nucleic acid, regardless of its origin) can be digested by a particular restriction endonuclease into a discrete set of restriction fragments. The DNA fragments that result from restriction endonuclease cleavage can be further used in a variety of techniques and can, for instance, be detected by gel electrophoresis or sequencing. Restriction fragments can be blunt ended or have an overhang. The overhang can be removed using a technique described as polishing. The term 'internal sequence' of a restriction fragment is typically used to indicate that the origin of the part of the restriction fragment resides in the sample genome, i.e. does not form part of an adapter. The internal sequence is directly derived from the sample genome, its sequence is hence part of the sequence of the genome under investigation.

The term "transposon" or "transposable element (TE)" or, "retrotransposon" refers to a DNA sequence that can change its position within the genome, sometimes creating or reversing mutations and altering the cell's genome size. Transposition often results in duplication of the TE. Transposable elements (TEs) represent one of several types of mobile genetic elements. TEs are assigned to one of two classes according to their mechanism of transposition, which can be described as either copy and paste (class I TEs) or cut and paste (class II TEs). Class I TEs are copied in two stages: first they are transcribed from DNA to RNA, and the RNA produced is then reverse transcribed to DNA. This copied DNA is then inserted at a new position into the genome. The reverse transcription step is catalyzed by a reverse transcriptase. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site.

As used herein, "Ligation" refers to the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case, the covalent joining will occur in only one of the two DNA strands.

"Adapters" are short double-stranded DNA molecules with a limited number of base pairs, e.g. about 10 to about 30 base pairs in length, which are designed such that they can be ligated to the ends of restriction fragments. Adapters are generally composed of two synthetic oligonucleotides that have nucleotide sequences which are partially complementary to each other. When mixing the two synthetic oligonucleotides in solution under appropriate conditions, they will anneal to each other forming a double-stranded structure. After annealing, one end of the adapter molecule is designed such that it is compatible with the end of a restriction fragment and can be ligated thereto; the other end of the adapter can be designed so that it cannot be ligated, but this need not be the case (double ligated adapters). Adapters can contain other functional features such as identifiers, recognition sequences for restriction enzymes, primer binding sections etc. When containing other functional features the length of the adapters may increase, but by combining functional features this may be controlled.

"Adapter-ligated restriction fragments" refer to restriction fragments that have been capped by adapters on one or both ends.

As used herein, "barcode" or "tag" refer to a short sequence that can be added or inserted to an adapter or a primer or included in its sequence or otherwise used as label to provide a unique barcode (aka barcode or index). Such a sequence barcode (tag) can be a unique base sequence of varying but defined length, typically from 4-16 bp used for identifying a specific nucleic acid sample. For instance 4 bp tags allow $4^4=256$ different tags. Using such an barcode, the origin of a PCR sample can be determined upon further processing or fragments can be related to a clone. Also clones in a pool can be distinguished from one another using these sequence based barcodes. Thus, barcodes can be sample specific, pool specific, clone specific, amplicon specific etc. In the case of combining processed products originating from different nucleic acid samples, the different nucleic acid samples are generally identified using different barcodes. Barcodes preferably differ from each other by at least two base pairs and preferably do not contain two identical consecutive bases to prevent misreads. The barcode function can sometimes be combined with other functionalities such as adapters or primers and can be located at any convenient position. A barcode is often used as a fingerprint for labeling a DNA fragment and/or a library and for constructing a multiplex library. The library includes, but not limited to, genomic DNA library, cDNA library and ChIP library. Libraries, of which each is separately labeled with a distinct barcode, may be pooled together to form a multiplex barcoded library for performing sequencing simultaneously, in which each barcode is sequenced together with its flanking tags located in the same construct and thereby serves as a fingerprint for the DNA fragment and/or library labeled by it. A "barcode" is positioned in between two restriction enzyme (RE) recognition sequences. A barcode may be virtual, in which case the two RE recognition sites themselves become a barcode. Preferably, a barcode is made with a specific nucleotide sequence having 0 (i.e., a virtual sequence), 1, 2, 3, 4, 5, 6, or more base pairs in length. The length of a barcode may be increased along with the maximum sequencing length of a sequencer.

As used herein, "primers" refer to DNA strands which can prime the synthesis of DNA. DNA polymerase cannot synthesize DNA de novo without primers: it can only extend an existing DNA strand in a reaction in which the complementary strand is used as a template to direct the order of nucleotides to be assembled. The synthetic oligonucleotide molecules which are used in a polymerase chain reaction (PCR) as primers are referred to as "primers".

As used herein, the term "DNA amplification" will be typically used to denote the in vitro synthesis of double-stranded DNA molecules using PCR. It is noted that other amplification methods exist and they may be used in the present invention without departing from the gist.

As used herein, "aligning" means the comparison of two or more nucleotide sequences based on the presence of short or long stretches of identical or similar nucleotides. Several methods for alignment of nucleotide sequences are known in the art, as will be further explained below.

"Alignment" refers to the positioning of multiple sequences in a tabular presentation to maximize the possibility for obtaining regions of sequence identity across the various sequences in the alignment, e.g. by introducing gaps. Several methods for alignment of nucleotide sequences are known in the art, as will be further explained below.

The term "contig" is used in connection with DNA sequence analysis, and refers to assembled contiguous stretches of DNA derived from two or more DNA fragments having contiguous nucleotide sequences. Thus, a contig is a set of overlapping DNA fragments that provides a partial contiguous sequence of a genome. A "scaffold" is defined as a series of contigs that are in the correct order, but are not connected in one continuous sequence, i.e. contain gaps. Contig maps also represent the structure of contiguous regions of a genome by specifying overlap relationships among a set of clones. For example, the term "contigs" encompasses a series of cloning vectors which are ordered in such a way as to have each sequence overlap that of its neighbors. The linked clones can then be grouped into contigs, either manually or, preferably, using appropriate computer programs such as FPC, PHRAP, CAP3 etc.

"Fragmentation" refers to a technique used to fragment DNA into smaller fragments. Fragmentation can be enzymatic, chemical or physical. Random fragmentation is a technique that provides fragments with a length that is independent of their sequence. Typically, shearing or nebulisation are techniques that provide random fragments of DNA. Typically, the intensity or time of the random fragmentation is determinative for the average length of the fragments. Following fragmentation, a size selection can be performed to select the desired size range of the fragments "Physical mapping" describes techniques using molecular biology techniques such as hybridization analysis, PCR and sequencing to examine DNA molecules directly in order to construct maps showing the positions of sequence features.

"Genetic mapping" is based on the use of genetic techniques such as pedigree analysis to construct maps showing the positions of sequence features on a genome The term "genome", as used herein, relates to a material or mixture of materials, containing genetic material from an organism. The term "genomic DNA" as used herein refers to deoxyribonucleic acids that are obtained from an organism. The terms "genome" and "genomic DNA" encompass genetic material that may have undergone amplification, purification, or fragmentation.

The term "reference genome", as used herein, refers to a sample comprising genomic DNA to which a test sample may be compared. In certain cases, reference genome contains regions of known sequence information.

The term "double-stranded" as used herein refers to nucleic acids formed by hybridization of two single strands of nucleic acids containing complementary sequences. In most cases, genomic DNA are double-stranded.

As used herein, the term "single nucleotide polymorphism", or "SNP" for short, refers to single nucleotide position in a genomic sequence for which two or more alternative alleles are present at appreciable frequency (e.g., at least 1%) in a population.

The term "chromosomal region" or "chromosomal segment", as used herein, denotes a contiguous length of nucleotides in a genome of an organism. A chromosomal region may be in the range of 1000 nucleotides in length to an entire chromosome, e.g., 100 kb to 10 MB for example.

The terms "sequence alteration" or "sequence variation", as used herein, refer to a difference in nucleic acid sequence between a test sample and a reference sample that may vary over a range of 1 to 10 bases, 10 to 100 bases, 100 to 100 kb, or 100 kb to 10 MB. Sequence alteration may include single nucleotide polymorphism and genetic mutations relative to wild-type. In certain embodiments, sequence alteration results from one or more parts of a chromosome being rearranged within a single chromosome or between chromosomes relative to a reference. In certain cases, a sequence alteration may reflect a difference, e.g. abnormality, in chromosome structure, such as an inversion, a deletion, an insertion or a translocation relative to a reference chromosome, for example.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, the term "endonuclease" refers to a family of enzymes that has an activity described as EC 3.1.21, EC 3.1.22, or EC 3.1.25, according to the IUBMB enzyme nomenclature. Site-specific endonucleases recognize specific nucleotide sequences in double-stranded DNA. Some sequence-specific endonucleases cleave only one of the strands in a duplex and are referred to herein as "nicking endonucleases". Nicking endonuclease catalyzes the hydrolysis of a phosphodiester bond, resulting in either a 5' or 3' phosphomonoester.

A "site-specific nicking endonuclease", as used herein, denotes a nicking endonuclease that cleaves one strand of a double-stranded nucleic acid by recognizing a specific sequence on the nucleic acid. The cleavage site or "nick site" of the phosphodiester backbone may fall within or immediately adjacent the recognition sequence of the site-specific nicking endonuclease.

Description

The present invention relates to innovative methods of DNA mapping and sequencing technology based on massively parallel sequencing with linked-paired-end sequencing libraries. The main concept of this current invention relies on fragmenting the whole genome so that the ends of the adjacent DNA fragments share the same sequences (referred to herein as linker sequences). These linked DNA fragments are then sequenced and the sequence reads can then be mapped back to the whole genome map and assembled.

In one aspect, the method of the invention comprises generating DNA fragments for sequencing at a specific sequence motif where the ends of adjacent DNA fragments share the same sequences (overlapping sequences). These overlapping sequences can be 50-250 bases long. In some embodiments, for fragments shorter than 1 kb, a direct sequencing and linking in the adjoining sequences provides direct linkage between and within fragments. In other embodiments, for fragments longer than 1 kb, linked-mate-end sequencing libraries are constructed to provide linkage between and within fragments up to 16 kb. Genetic variations found within the overlapping sequences are then used to separate the two haplotype-resolved reads and generate scaffolds anchored at specific sequence motifs for subsequent de novo based sequence assembly. The methods of this invention preserve linkage identity, enable haplotype information and facilitate the de novo sequence assembly with short-read shotgun sequencing. The present invention enables achieving high-quality, low-cost de novo assembly of complex genomes and capturing various scales of sequence contiguity information.

Several methods are disclosed herein for generating sequence-linked DNA fragments from genomic DNA molecules or cloned DNA molecules. These methods include:
1. nicking-flap-nicking scheme
2. nicking-flap-cutting scheme
3. restriction enzyme based scheme
4. in vitro transposition based scheme In one embodiment, the genomic DNA is fragmented by exposing the double-stranded DNA polymer to a nicking endonuclease (also referred to as nickase), or a restriction endonuclease. The enzymes can be highly sequence-specific, meaning that they bind to a particular sequence of bases or motifs, with a high degree of specificity. Nickases are available, e.g., from New England BioLabs. The generated DNA fragments can be a size of 10 kb, 50 kb, 100 kb to about 1000 kb or more.

In one embodiment, the fragmentation sites of the genomic DNA correspond to the recognition sites of the nicking endonuclease irrespective of the nucleotide sequences that flank the recognition site. Therefore, the flanking sequences depicted in FIGS. 1-7; FIG. 8A; FIGS. 10-14; FIG. 16; FIGS. 18-20; FIG. 25 and FIGS. 29A-29B are presented herein for illustration only and as such have no bearing on the essence of the invention and should not therefore be required to be listed in the sequence listing per 37 C.F.R. 1.821-1.825.

In some other aspects of this invention, the DNA fragments can be amplified and purified by methods known in the art.

Nicking-Flap-Nicking Scheme

In one embodiment, a nicking-Flap-nicking scheme is applied to generate sequence-linked DNA fragments from genomic DNA molecules or cloned DNA molecules. In one aspect of the present invention, this scheme includes a method of contacting the double-stranded DNA template with a first nicking endonuclease to form a nick at a sequence-specific nicking location on the first DNA strand. In another aspect, the nicking-Flap-nicking scheme involves conducting a base extension reaction on the first DNA strand along a corresponding region of the second DNA strand, wherein the reaction starts at the nick and progresses toward the 3' end of the first DNA strand thereby forming a single-stranded flap on the double-stranded DNA template adjacent to the sequence-specific nicking location. In a further aspect of this invention, the nicking-flap-nicking scheme involves contacting the double-stranded DNA template with a second nicking endonuclease to form a cut at a sequence-specific location thereby generating two cut DNA fragments wherein the single stranded flap previously synthesized can hybridize on the complementary strand of one of the two fragments of the cut DNA. In yet a further aspect of this invention, a base extension reaction is conducted on the second DNA strand of the second fragment along a corresponding region of the first DNA strand, wherein the reaction starts at the nick and progresses toward the 3' end of the first DNA strand thereby forming a double-stranded DNA fragment sharing common linker sequences with the first double-stranded DNA fragment.

Site-specific nicking endonuclease, also referred to as nickase, nicks the backbone of a double-stranded DNA in a sequence specific manner and cleaves only one strand of double-stranded DNA at the recognition site.

In some embodiments relevant nickases include, but are not limited to, Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII, used either alone or in various combinations. Other suitable nicking endonucleases are available from commercial sources, including New England Biolabs and Fermentas. The recognition sequences vary from one to the other and are well known in the art. Some site-specific nicking endonucleases along with their features are summarized herein.

The nickase Nb.BbvCI is derived from an *E. coli* strain expressing an altered form of the BbvCI restriction genes [Ra+:Rb(E177G)] from Bacillus brevis.

The nickase Nb.BsmI is derived from an *E. coli* strain that carries the cloned BsmI gene from Bacillus stearothermophilus NUB 36.

The nickase Nb.BsrDI is derived from an *E. coli* strain expressing only the large subunit of the BsrDI restriction gene from Bacillus stearothermophilus D70.

The nickase Nb.BtsI is derived from an *E. coli* strain expressing only the large subunit of the BtsI restriction gene from Bacillus thermoglucosidasius.

The nickase Nt.AlwI is an engineered derivative of AlwI which catalyzes a single-strand break four bases beyond the 3' end of the recognition sequence on the top strand. It is derived from an *E. coli* strain containing a chimeric gene encoding the DNA recognition domain of AlwI and the cleavage/dimerization domain of Nt.BstNBI.

The nickase Nt.BbvCI is derived from an *E. coli* strain expressing an altered form of the BbvCI restriction genes [Ra(K169E):Rb+] from Bacillus brevis.

The nickase Nt.BsmAI is derived from an *E. coli* strain expressing an altered form of the BsmAI restriction genes from Bacillus stearothermophilus A664.

The nickase Nt.BspQI is derived from an *E. coli* strain expressing an engineered BspQI variant from BspQI restriction enzyme.

The nickase Nt.BstNBI catalyzes a single strand break four bases beyond the 3' side of the recognition sequence. It is derived from an *E. coli* strain that carries the cloned Nt.BstNBI gene from Bacillus stereothermophilus 33M.

The nickase Nt.CviPII cleaves one strand of a double-stranded DNA substrate. The final product on pUC19 (a plasmid cloning vector) is an array of bands from 25 to 200 base pairs. CCT is cut less efficiently than CCG and CCA, and some of the CCT sites remain uncleaved. It is derived from an *E. coli* strain that expresses a fusion of Mxe GyrA intein, chitin-binding domain and a truncated form of the Nt.CviPII nicking endonuclease gene from Chlorella virus NYs-1.

In some embodiments, more than one site-specific nicking endonuclease, e.g. two, three, or more different types of site-specific nicking endonucleases are used. In some specific embodiments, a site-specific nicking endonuclease that does not have any variable nucleotide adjacent to its nick site such as Nt.BbvCI or Nb. BbvCI is used.

In certain embodiments, the nicking is suitably effected at one or more sequence-specific locations, although the nicking can be effected at one or more non-specific locations, including random or non-specific locations.

In some embodiments, incorporation of replacement bases into the first strand (i.e., the nicked strand) of double-stranded DNA comprises contacting DNA with a polymerase, one or more nucleotides, a ligase, or any combination thereof. Other methods for replacing the "peeled-away" bases present in the flap will also be known to those of ordinary skill in the art.

The first DNA strand is suitably extended along the corresponding region of the second DNA, which region is left behind/exposed by the formation of the flap. In other embodiments, the polymerase acts concurrently with a nickase that gives rise to a flap. The incorporation of these replacement bases can be conceptualized as filling-in the gap left behind by the formation and "peeling-up" of the flap. By filling in the gap, the position formerly occupied by the flap is occupied by a set of bases that suitably has the same sequence as the bases located in the flap. The filling prevents re-hybridization of the flap to the second stand of DNA to which the flap was formerly bound.

In some embodiments, the generated flap is about 1 to about 1000 bases in length. Typically, a flap is from about 20 to about 100 bases in length, or even in the range of from about 30 to about 50 bases.

In further embodiments, the strand extension may involve different polymerases (such as proofreading polymerases, Vent polymerases, 5'>3' exo-polymerase (Klenow fragment) or T4 polymerase), ligases and/or nucleotide composition to accommodate the various needs. In certain cases, the nucleotide composition facilitates multi-color labeling, in which there may be at least two, three, or four distinguishably labeled nucleotides. In further cases, the detectable label of a nucleotide comprises a tag that emits a color or a non-fluorescent tag that is further processed for visualization. In yet further embodiments, the nucleotide mixture comprises phosphorothioated nucleotides, e.g., nucleoside alpha-thio-triphosphates (also known as alpha-thionucleoside triphosphates).

Nicking-Flap-Cutting Scheme

In another embodiment of the invention, a nicking-Flap-cutting scheme is applied to generate sequence-linked DNA fragments. In one aspect of the present invention and as described previously herein, this scheme features a method of contacting the double-stranded DNA template with a first nicking endonuclease to form a nick at a sequence-specific nicking location on the first DNA strand. In another aspect, and as previously described for the nicking-flap-nicking scheme, the nicking-Flap-cutting scheme involves conducting a base extension reaction on the first DNA strand along a corresponding region of the second DNA strand, wherein the reaction starts at the nick and progresses toward the 3' end of the first DNA strand thereby forming a single-stranded flap on the double-stranded DNA template adjacent to the sequence-specific nicking location. In a further aspect of this invention, the nicking-flap-cutting scheme involves contacting the double-stranded DNA template with a T7 endonuclease to form a cut at a sequence-specific location thereby generating two cut DNA fragments, wherein the single stranded flap previously synthesized forms an overhang on one of the two fragments of the cut DNA. In yet a further aspect of this invention, a base extension reaction is conducted on the fragment with the overhang stranded flap along the corresponding region of single stranded flap, wherein the reaction starts at the nick site of the T7 endonuclease and progresses toward the end of the stranded flap, thereby forming a blunt end double-stranded DNA fragment sharing common linker sequences with the other double-stranded DNA fragment generated during the T7 endonuclease cut. The choice of T7 endonuclease in the nicking-Flap-cutting scheme of the present invention is critical as this enzyme recognizes and cleaves non-perfectly matched DNA, cruciform DNA structures, Holliday structures or junctions, heteroduplex DNA and more slowly, nicked double-stranded DNA. In some aspects of this invention, the T7 endonuclease detects and/or cleaves the heteroduplex and nicked DNA generated during the very first step. The cleavage site is at the first, second or third phosphodiester bond that is 5' to the mismatch. The nicking may also be accomplished by other enzymes that effect a break or cut in a strand of DNA. Such breaks or nicks can also be accomplished by exposure to electromagnetic radiation (e.g., UV light), one or more free radicals, and the like. Nicks may be effected by one or more of these techniques.

In a further aspect of this invention, a base extension reaction is conducted on the fragment with the flap overhang. The extension is conducted the corresponding region of single stranded flap, wherein the reaction starts at the nick site of the T7 endonuclease and progresses toward the end of the stranded flap thereby forming a blunt end double-stranded DNA fragment sharing common linker sequences with the other double-stranded DNA fragment.

Restriction Enzyme Based Scheme

In one embodiment of the invention, a restriction enzyme based scheme is applied to generate sequence-linked DNA fragments. In one aspect of the present invention this scheme features a method of contacting a restriction endonuclease to form overhang double stranded cuts of the DNA at a sequence-specific location. In another aspect of the invention, a base extension reaction is conducted on the fragments of the overhang DNA thereby forming blunt end double-stranded DNA fragments sharing common linker sequences between each other.

In certain embodiments, the restriction endonuclease comprises one or more Type IIb endonucleases that cleave both strands on both sides of a double-stranded DNA substrate. The recognition site of these enzymes is defined, symmetric and short distance away. The cleavage generates 3' overhangs that are of interest in the current invention for producing the linker sequences. The recognition site of these endonucleases is well known in the art.

Non limiting example of Type IIb endonucleases that can be used in the methods of the invention are BaeI, BcgI, Bsp24I, CjeI, and CjePI.

In other embodiments, as performed in the previously described schemes, a base extension reaction is conducted on the fragment with the overhanging fragment thereby allowing the formation of blunt end double-stranded DNA fragments sharing common linker sequences between each other.

In Vitro Transposition Based Scheme

In one embodiment of the invention, an in vitro transposition based scheme is applied to generate linked-paired-end nucleic acid fragment from a DNA sample. Transposons are mobile genetic elements and have been utilized as essential tools in genetics over the years.

Transposases catalyze the random insertion of excised transposons into DNA targets with high efficiency. In the present invention, a transposon library is generated, such that each transposase binds to a unique oligo sequence. When inserted into DNA templates, the ends share the same sequences only at that specific locus. In one aspect, this in vitro transposition scheme features a method of contacting the double-stranded DNA template with a transposase thereby catalyzing the insertion of excised transposons into DNA targets. In another aspect, a base extension reaction is conducted on the inserted transposons thereby incorporating nucleotide barcodes within the DNA fragments and therefore allowing the DNA fragments to share common linker sequences between each other.

The mode and order of contacting the genomic sample with the enzyme of choice, i.e., site-specific nicking endonuclease, T7 endonuclease, restriction enzymes or transposase, varies depending on the assay conditions. In some embodiments, two, three or more different enzymes with various combination of flap/fragment are used. In yet other embodiments, the enzyme may be added to a sample comprising the genomic DNA. In further embodiments, the sample comprising the genomic DNA is added to a solution containing the enzyme. In certain embodiments, the genomic sample comprising the double-stranded DNA is contacted with the enzyme, the polymerase, and the nucleotide composition all at the same time. Conditions and reagents suitable for the nicking/cutting activity of enzymes are known to one of skilled in the art. Exemplary methods and experimental conditions suitable for an active site-specific nicking endonuclease may be found in Jo K et al. (2007) PNAS 104:2673-2678 and Xiao M et al. (2007) Nucleic Acids Res. 35:e16.

The invention includes methods relating to DNA mapping and sequencing, including methods for making linked-paired-end sequenced genomic DNA fragments, methods of analyzing the nucleotides sequences of the linked fragments and identifying multiple sequence motifs or polymorphic sites, and methods of establishing sequence contiguity across the whole genome. These methods generate continuous base by base sequencing information, within the context of the DNA map allowing de novo whole genome mapping. Compared with prior art methods, the present methods of DNA mapping provide improved sequence contiguity across the whole genome, and achieve high-quality, fast, and low-cost de novo assembly of complex genomes.

In one embodiment, the generated linked-paired-end fragment are directly shotgun sequenced. This sequencing procedure involves diluting the linked-paired-end fragments, amplifying them by PCR and sequencing them.

In another embodiment, the generated linked-paired-end fragment are processed further in a library for sequencing. Various sequencing platforms are known in the art. The choice of a platform may be based on the user's and experiment's requirements. In some embodiments, the sequencing method is a high throughput next-generation method. Non limiting example of massively parallel signature sequencing platforms are Illumina sequencing by synthesis (Illumina, san Diego Calif.), 454 pyrosequencing (Roche Diagnostics, Indianapolis Ind.), SOLiD sequencing (Life Technologies, Carlsbad, Calif.), Ion Torrent semiconductor sequencing (Life Technologies, Carlsbad, Calif.), Heliscope single molecule sequencing (Helicos Biosciences, Cambridge, Mass.), and Single molecule real time (SMRT) sequencing (Pacific Biosciences, Menlo Park, Calif.).

In certain aspects of the invention, the library preparation for sequencing comprises the following main steps: (a) circularizing the paired-end linked fragments, (b) fragmenting, (c) size selecting the fragments of interest, and (d) ligating adaptors at one or both end(s) of the fragments for single or paired-end sequencing. In further aspects, known barcoded nucleotide adaptors are incorporated to the adaptors ligation step (d). In other aspects, the sequencing library construction and adaptors/barcodes addition increases both sides of the linked-paired-end fragments by 50, 100, 150, 200 or more bases.

In another embodiment, the sequenced linked-paired-end fragments of the invention are useful for whole genome mapping. By determining the positions of the sequenced linkers/adaptors within each fragments with respect to a reference known genomic DNA backbone, the distribution of the linked-paired-end fragments can be mapped accurately base by base and assembled. This method is illustrated elsewhere herein in the identification of lambda phage DNA molecules and human BAC clones. In yet another embodiment, the sequenced linked-paired-end fragments of the invention are useful for haplotype-scaffold-sequencing (HSS) wherein the sequence contiguity across the whole genome is established allowing de novo haplotype sequence assembly of haploid human genomes. In a further embodiment, the haplotype sequence assembly comprises the human major histocompatibility (MHC) region.

In another embodiment, the sequencing information from the linked-paired-end fragments allow a broad range of computational analysis of the sequence reads. The wide variety of analysis can be appreciated and performed by those skilled in the art. Non-limiting examples where the sequenced linked-paired-end fragments are used include capturing various scales of sequence and structural variation, haplotypes, methylation pattern, epigenomic pattern, location of CpG islands, single nucleotide polymorphisms (SNPs), copy number variations (CNVs), introns retentions and other nucleotides configurations for coding and non-coding elements.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the experiments disclosed herein are now described.

Materials and Methods

Lambda DNA is from New England BioLabs (NEB). Nicking enzymes, Klenow polymerase, Taq Polymerase, T7 Endonuclease, Taq ligase and other enzymes are from NEB. Human BAC clones are form Children's Hospital Oakland Research Institute. Human genomic DNA samples are from Coriell research Institute. DNA oligos and random hexamer are from Integrated DNA technology (IDT). In nick-flap-nick reaction, The DNA first are incubated with Nb.BbvcI nicking enzymes at the enzymes' optimal temperature and their suggested buffer. After nicking, single stranded flap sequences are introduced by incubating nicked DNA with certain polymerases lack 5'-3' exonuclease activity such as Klenow Exo-polymerase. In the last step, Nt.bbvcI is employed to nick the opposite strand to the Nb.BbvCI. In nick-flap-T7 Endonuclease reaction, the DNA is first incubated with nicking enzymes at the enzymes' optimal temperature and their suggested buffer. After nicking, single stranded flap sequences are introduced by incubating nicked DNA with certain polymerases lack 5'-3' exonuclease activity such as KlenowExo-polymerase. In the last step, T7 endonuclease is employed to nick the opposite strand to the flap sequences.

Example 1: Nicking-Flapping-Nicking Scheme

Figure 2:
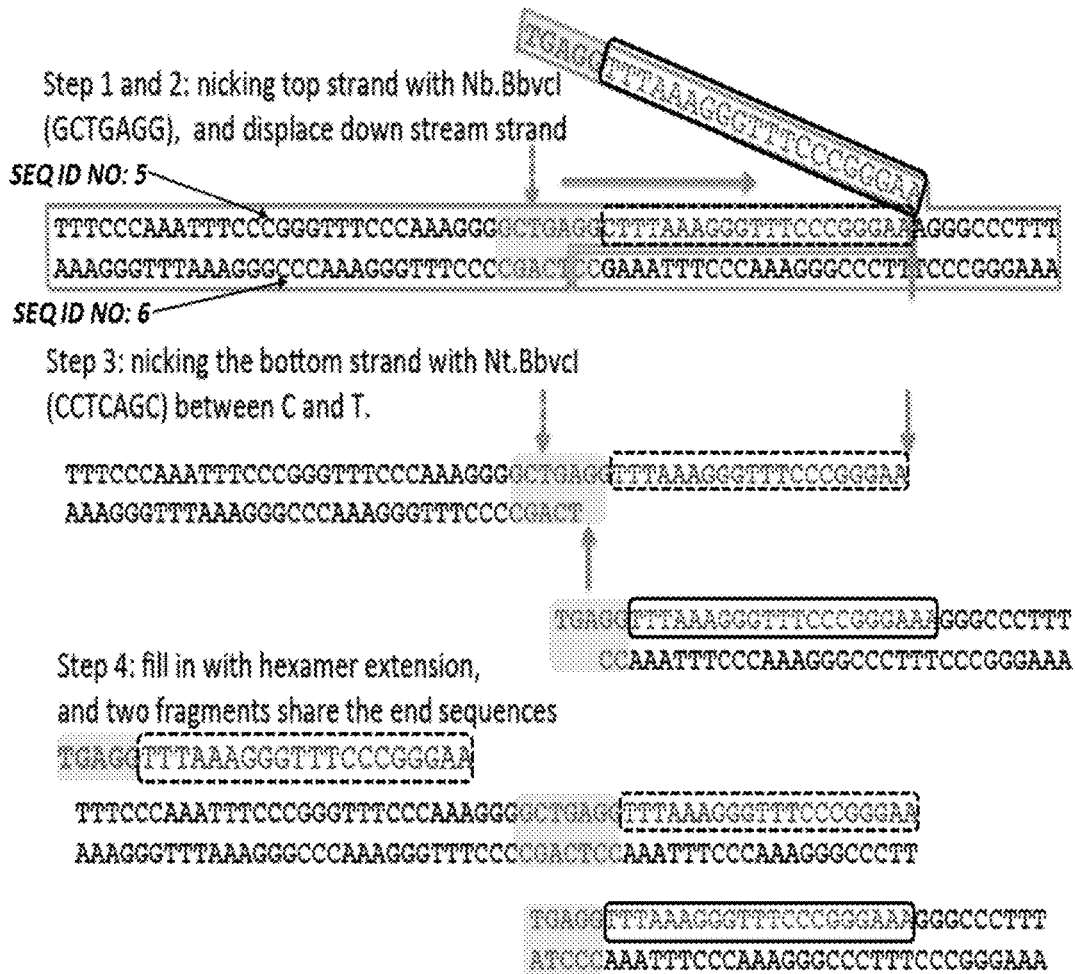
FIG. 2 is a schematic demonstrating one scheme of the present invention which is called the "Nick-Flap-Nick" scheme (SEQ ID NOs: 5-6). A nickase such as Nb.BbvCI is used to generate single strand nicks in the target DNA (The enzyme recognition site is in grey shaded area). The nicks are used as priming sites for DNA synthesis by a DNA polymerase with strand displacement activity, which creates a flap. Next, another nickase, such as Nt.BbvCI, is used to generate a single strand nick on the opposite strand at the same recognition sequence as the first nickase. The adjacent fragments melt apart and the flap re-anneals to its complement strand. This leaves a long 3' overhang on one fragment. To preserve the sequence of the overhang, it is converted to dsDNA any number of methods available in the art.

The description of DNA chemistry scheme: The nicking-flap-nicking scheme includes four steps (FIG. 2). This method of overlap sequence generation starts with introducing nicks in dsDNA at specific sequence motifs recognized by nicking endonucleases which cleave only one strand of a dsDNA substrate (Morgan et al., Biol Chem., 381, 1123-1125). In this case, Nb.BbvcI recognizes GCTGAGG (in grey shaded area) and nicks the DNA molecules between the C and T bases (dashed grey arrow). Klenow polymerase then synthesizes a new DNA strand (bases surrounded by a dashed black box) and at the same time displaces the original strand (bases surrounded by a solid black box). Through all this, a flap sequence, surrounded by a solid black box, is generated, and the original nicking site is pushed downstream 50-100 bases (solid grey arrow). In the next step, a Nt.BbvcI nicking enzyme is used to recognize CCTCAGC of the bottom strand (in grey shaded area) and make a nick between C and T base. After being heated to 75 degree, the double stranded DNA molecules break into two fragments between the two nicks (solid grey arrows). The left fragment contains a newly synthesized single-stranded 50-100 bases (bases surrounded by a dashed black box) at its 3' end. The flap sequence drops back and hybridizes to form the structure described in the FIG. 2. This way, the 3' end of the left fragment will share the same 50-100 bases with the 5' end of the right fragment. During the final step, random hexamers hybridize the single stranded sequences and E. coli polymerase converts the single stranded sequences into double-stranded structures.

The harmony of the first two steps (FIG. 2) is critical to the success of this procedure: Controlling the extension from nicking sites and specifically cutting the nicking sites with T7 endonuclease. By testing different polymerases, different amounts of polymerases, different amounts of nucleotides and different incubation times, the extension step was successfully controlled to up to 500 bases. A mutant T7 endonuclease, which specifically cuts opposite from the flap, was obtained thus minimizing random nicks. To further minimize the random nicks and preserve the longer flap sequences, a proprietary procedure was developed. The typical high throughput sequencing reads with a nicking enzyme Nt.BstNBI are shown in FIG. 29A. BstNBI nickase nicks four bases away from the BstNBI recognition motif (GAGTC, highlighted by a grey shaded area). The DNA sequences surrounded by a solid black box are generated through polymerase extension, and may have various extension lengths. While the flap sequences shown in black, will all start four bases away from GAGTC. One of the typical sequence alignments from Illumina MiSeq reads is generated by the Integrated Genome View (IGV) and shown in FIG. 29B, and fits the predicted patterns. These sequence alignment patterns are enriched and consistent through all nicking sites based on the sequencing results of this invention. The overlap sequences information is critical and is subsequently used for the construction of the haplotype resolved scaffold.

Four different end structures are generated through the combination of the recognition sequence motifs (FIGS. 3-6). A separate sequencing library can also generated by reversing the sequential use of the nicking enzymes, applying Nt.BbvcI first and then Nb.BbvcI. By combining these two libraries, one can easily produce 100 bp linker sequences (FIG. 7). DNA chemistry results: Lambda DNA was used as a model system to demonstrate the optimization of critical parameters for linker-sequence generation. The distribution of the seven recognition sites of nick endonuclease Nb.BbvC (either CTGACG or its complimentary GCTGAGG) of lambda-DNA is shown in FIG. 8A. The seven sites are at 8016 bp, 18151 bp, 18467 bp, 31226 bp, 31840 bp and 35815 bp respectively. There are 8 fragments generated between those seven recognition sites with fragment length as 8 kb, 10 kb, 316 bp, 12 kb, 308 bp, 614 bp, and 4 kb. For example, the fragment length between the sites 18467 bp and 18467 bp is 316 bp. For this particular fragment, the 5' end has CCTCAGC (−) and the 3' end possesses a GCTGAGG (+). As a result in the 5' end and 3' end structures as indicated by the boxed sequences on FIG. 7.

For this scheme to work, several critical parameters require optimization. These parameters include the amount of nicking enzyme, the incubation time during the first nicking reaction, the type and amount of polymerase, the nucleotide concentration during flap generation reaction, and the amount of enzymes during the second nicking reaction. FIG. 8B and FIG. 8C demonstrate that the optimized nucleotide concentration should be around 50-150 nM for lambda DNA. 5 units of nicking endonuclease are appropriate during the first and second nicking reactions to generate a mapping. The length of each fragment agrees well with the in silico prediction. FIG. 8D is a fluorescent gel electrophoresis image of two Cy3 conjugated oligonucleotide probes complementary for two specific 3' overhangs near BbvCI sites in the Lambda phage genome. The two fluorescent probes are designed to hybridize to the single stranded structures at the ends of the 4 kb fragment and 10 kb fragment. The gel shows the presence of the single stranded DNA structures at the ends 3 kb and 10 kb fragments. The lambda DNA results with a human BAC clone DNA confirm its utility as another model system. Under optimized condition for human genome, the linked fragments are generated as predicted (FIG. 9A). The fluorescent gel image also confirms the presence of the linker sequences at the ends of each fragment (FIG. 9A). In these sets of experiments, the procedure of converting single stranded DNA structure at each end to double-stranded DNA with random hexamer hybridization and extension was optimized. FIG. 8B shows there is no difference in fragment size distribution with and without hexamer treatment. Moreover, with hexamer treatment, the probes cannot be hybridized to the ends because no single-stranded DNA structure is available (FIG. 9C).

Example 2: Nicking-Flapping-Cutting Scheme with T7 Endonuclease

Description Of DNA Chemistry Scheme: The nicking-flap-cutting scheme also includes four steps (FIG. 10). The first two steps are the same as they were in the nicking-flapping-nicking scheme. During the third step, however, T7 endonuclease is used to cut the opposite strand across the nicking sites. This generates a slightly different structure of 5' single stranded DNA overhang instead of 3' overhang in nicking-flapping-nicking scheme. In the final step, the single stranded structures are simply filled through polymerase extension. Four different end structures are generated based on the combination of the recognition sequence motifs (FIGS. 11-14).

DNA Chemistry results: Again, lambda DNA was used as a model system to demonstrate the optimization of critical parameters for linker-sequence generation. FIGS. 15A-15C show that the same DNA fragment pattern is generated in nicking-flapping-cutting scheme as in the nicking-flapping-nicking scheme, including 12 kb, 10 kb, 8 kb, 600 bp and 300 bp. But the same fluorescent probes hybridize to 12 kb and 10 kb instead of 8 kb and 3.9 kb in nicking-flapping-nicking scheme. This is in total agreement with the prediction and reflects the different single stranded DNA structures at the ends between nicking-flapping-nicking scheme and nicking-flapping-cutting scheme. In this chemistry scheme, the currently available nicking enzymes are Nb.BbvCI, Nt.BbvCI, Nt.BsmI, Nt.BsmAI, Nt.BstNBI, Nb.BsrDI, Nb.BstI, Nt.BspQI, Nt.Bpu10I and Nt.Bpu10I.

Example 3: Restriction Enzyme Scheme

Certain types of restriction enzymes cut the double stranded DNA molecules several to hundred bases away from the recognition sequences as shown in FIG. 16 (between the arrows), which results in two fragments sharing 5 bases at both 5' and 3' ends. In another example, the restriction enzyme BaeI can be engineered for this purpose. After the DNA fragment has been cut, both ends will share up 5-40 bases of linker-sequences. The limitation of this approach is the short length of the linker.

Example 4: In Vitro Transposition Based Scheme

Transposons are mobile genetic elements and have been utilized as essential tools in genetics over the years. Transposases catalyze the random insertion of excised transposons into DNA targets with high efficiency. Using this method, a transposon library was generated, such that each transposase binds to a unique oligo sequence. When inserted into DNA templates, the ends share the same sequences only at that specific locus (FIG. 17).

Example 5: De Novo Haplotype-Resolved Whole Genome Mapping and Sequencing with Linked DNA Fragments De novo whole genome mapping: Linked-paired-end sequencing library was constructed using linked DNA fragments. Sequencing reads from such libraries were then used for de novo whole genome mapping (whole genome mapping by sequencing). The whole genome mapping by sequencing starts with breaking long dsDNA (>50 kb) molecules into smaller fragments and generating various sequences at the ends of each fragments such that the ends (5' and 3') of the adjacent fragments share more than 50 bases. These shared sequences are called "linker sequences" link neighboring DNA fragments. Three such fragments with their linker sequences are shown in FIG. 18. Next, each fragment is circularized so that the 5' end of each fragment joins, through DNA ligation, to the 3' end. Three such circular DNA molecules are shown in FIG. 19. The three molecules in FIG. 19 correspond to the three linked DNA fragments in FIG. 18. More than 100 bases surround the linker sequence at both directions (paired-end sequence, represented as rectangles in FIG. 19. Together with the linker sequences, the 100 bases are sequenced under massively parallel sequencing platforms. Paired-end sequences will be used to jump across the genomes, while the linker sequences are used to link these jumping libraries (FIG. 20). This way, a whole genome map, including 300 bp sequence information surrounding the nicking endonuclease recognition motifs, can be constructed.

This invention, using a simple technique for mapping complex regions or whole genomes, facilitates the de novo sequence assembly with long-range scaffolding information and structural variation analysis.

Genome mapping results: both lambda and human BAC clone maps were obtained. In FIG. 20, the three longest fragments from lambda DNA can be circularized and while there are no PCR products from the linear DNA, PCR products can be generated using circularized molecules, (FIG. 21). FIGS. 22A-22C show the sequencing results of lambda DNA map. Similar results are obtained with human BAC clone DNA (FIG. 23).

Example 6: Whole Genome Mapping by Haplotype Scaffold Sequencing (HSS) Provides High Specificity, High Resolution and Wide Genome Coverage The nick-flap scheme of linked-paired-end sequencing map provides high resolution, high specificity and high human genome coverage. The number and size of the restriction DNA fragments represent the resolution. To determine the resolution, the size distribution of Nt.BbvcI generated fragments in the human reference genome HG19 (2009) was analyzed in silico. There is a total of 1,395,211 fragments (FIG. 24). On average, there are one fragment over 2.15 kb and 1,100 longer fragments (>30 kb), which represents 1% of the genome. The reduced representation in the sequencing results may be due to the less efficient circularization of longer fragments. Overall, the whole genome map constructed by haplotype scaffold sequencing (HSS), based on the linked-paired-end sequencing methods of this invention, has about 2 kb resolution. This is 5 times better than optical mapping (Lam et al., Nature Biotechnology, 30, (8): p. 771-776, 2012). More importantly, the genome mapping of this current invention provides higher information content than optical mapping. In this invention, at least 300 pb of the map are sequenced around the Nt.BbvcI recognition sites, while in optical mapping technologies, only 6-8 bps are sequenced at the enzyme recognition motif.

Each linker sequence has about 57-207 bases. It was tested if the linker sequence is highly specific in representing its original DNA fragments and if it is unique enough to join two fragments specifically. The analysis of the results showed that this is indeed the case. FIG. 24 indicates that with 57 bases linker-sequence, 82% are unique. With 107 bases, 99.1% are unique across the whole genome, which is capable of linking any two adjacent fragments. As such the map is highly specific and can provide high coverage of the human genome. Not only are linker-sequences from the non-repetitive sequences highly specific, but the linker-sequence from the repetitive sequences are also highly specific. Half of the human genome is composed of repetitive DNA. Also of note, when the nickase Nt.BstNBI is used, 50 bp linker sequences are sufficient to reach 96.2% uniqueness across the whole human genome.

As discussed elsewhere herein, in order to assemble the haplotype resolved scaffold, the overlap sequences between adjacent fragments have to be unique. In another in silico analysis, all the overlap sequences (100 bp or 200 bp respectively) at the nickase recognition site were first identified based on the HG38 human reference genome (2013). Then, the pairwise comparison of all overlap sequences was performed and the percentage of those that are unique (i.e. with only one copy among all overlap sequences) was computed. The results are summarized in Table 1 below. At 100 bp, over 97% of overlap sequences were unique for all the nickases. If the length of the overlap sequence was increased to 200 bp, nearly 99.5% of overlap sequences would become unique (Nt.BstNBI) which can result in 99.5% scaffold coverage of human genome.

Thus the high specificity of linker-sequences for the repetitive DNA fragments allows this technology to analyze the structure in repetitive regions of the genome.

TABLE 1

| Nickase (recognition) | Total sites (Scaffold resolution) | Linker sequence length | |
|---|---|---|---|
| | | 100 bp | 200 bp |
| Nt.BspQI (GCTCTTC) | 370,000 sites (9 kb) | 97.0% | 98.4% |
| Nt.BbvCI (CCTCAGC) | 1.4 million sites (2.2 kb) | 97.0% | 98.2% |
| Nt.BsrDI (GCAATG) | 1.4 million sites (2.2 kb) | 96.4% | 97.9% |
| Nb.BtsI (GCAGTG) | 3 million sites (1 kb) | 97.2% | 98.6% |
| Nt.BstNBI (GAGTC) | 3.5 million sites (800 bp) | 97.8% | 98.5% |

Example 7: The Haplotype Scaffold Sequencing (HSS) Method is Cost Effective

The linked-paired-end sequencing-map described in the present invention requires sequencing only a fraction of the whole genome, as only the sequences surrounding the nickase recognition sequence need to be sequenced. For example, the Nt.BbvcI map has about 1.4 million fragments, and on average 300 bases will be sequenced on each fragment. 500 million bases will be sequenced for a human genome.

The Nt.BspQI has fewest nicking sites compared to other nickases. If 250 bp are to be sequenced around nicking sites, 3 Gb sequence reads would generate 30× coverage to construct the whole genome scaffold. However, 12% of genome needs to be covered with over 20 kb mate-pair library, which is more difficult to produce. Nt.BstNBI and Nt.BtsI would generate a much denser scaffold. It also requires shorter mate-pair library, because only 0.0003% of the sequencing fragments are over 20 kbp. The modeling of the present invention indicates that it would require 20 Gb sequencing reads to generate 30× coverage for Nt.BstNBI and Nt.BtsI. The other two enzymes Nt. BsrdI and Nt.BbvcI would fall in between. The sequencing throughput requirement for this invention is well within the capacity of MiSeq or HiSeq platforms (Illumina, CA) or Ion Torrent (Life technologies, CA) desktop sequencers. Thus, with current sequencing platforms, haplotype scaffold sequencing (HSS) methods based upon the linked-paired-end sequencing methods of this invention are extremely cost effective.

Example 8: The Whole Genome Mapping by Sequencing Provides Haplotype Resolved Whole Genome Maps As genome mapping produces data on molecules hundreds of thousand base pairs long, it can be particularly valuable for long-range haplotype analysis. FIG. 25 details the analysis procedure for constructing long haplotypes by linking the phase information of the SNPs in the 100 bp linker-sequences. For 4.6 Mb human MHC region, the methods of this invention generate one haplotype block to cover whole 4.6 Mb region using nickase Nt.BstNBI (FIG. 26).

Two parameters determine the success of constructing continuous haplotype blocks: the density of the genetic variations and the density of the nicking endonuclease's sequence motifs. There should be at least a single heterozygous variation within overlap sequences (~500 bp) from the nicking site, and the mate-pair library should be long enough to be linked to the next nicking site also containing a heterozygous variation. In an in silico analysis (FIG. 30), the ability of the methods of this invention for constructing continuous haplotype blocks was demonstrated using a data set from Sanger center's MHC haplotype project (Horton et al., Immunogenetics 60(1):1-18, 2008). First, two artificial MHC diploid genomes, COX/PGF and DBL/SSTO, were constructed by joining respective haplotypes. Then all the Nt.BstNbI nicking sites containing at least a single heterozygous variation within 500 bp extension were located. The adjacent heterozygous variations can be phased if they are within 12 kb which is the maximum length of jumping mate-pair library that can be constructed in the current protocol of the present invention. The continuous haplotype blocks are shown in FIG. 30 as a straight line, and the breaks between haplotype blocks are shown as various symbols. For the DBL/SSTO sample, the longest continuous haplotype block is over 2.3 Mb, and the longest haplotype block is 1.1 Mb for the COX/PGF sample. The break in the haplotype is mainly due to the fact there is no SNP within 12 kb of the maximum jumping library. One can simply increase the length of the jumping library to 20 kb to create a single continuous library in the human major histocompatibility (MHC) region.

Example 9: De Novo Whole Genome Sequencing

Linked DNA fragments can also be directly shotgun sequenced. In shotgun reading, the linked DNA fragments are diluted and amplified. The amplified PCR products are then subject to regular shotgun sequencing. The sequencing reads are then assembled according to the whole genome map generated with linked DNA fragments (FIGS. 27A-27B). Genome mapping produces data on molecules hundreds of thousands base pairs long. Therefore, this method is useful for long-range structural variation analysis. Examples of large scale inversions (500 kb) and insertions (33 kb) can be detected (FIG. 28).

The human major histocompatibility (MHC) region of a DNA sample was sequenced using the HSS method of this invention. A total of 2 million pair-end reads were generated for fragments between 500-1000 bp long. The average length of overlapping sequence of the above paired-end library is above 80 base pairs. A total 700,000 mate-pair reads were generated for fragments above 1 kb long. The average overlapping sequences in these libraries were above 200 bp. This data is used to develop computer algorithm, that can generate haplotype resolved de novo MHC sequence assembly. As an example, a 4 kb of such sequence assembly is shown in FIG. 31.

Summary of the Methods of the Invention: Generation and Sequencing of Linked-Paired-End Fragments and their Advantages Over Current Technologies.

Figure 1:
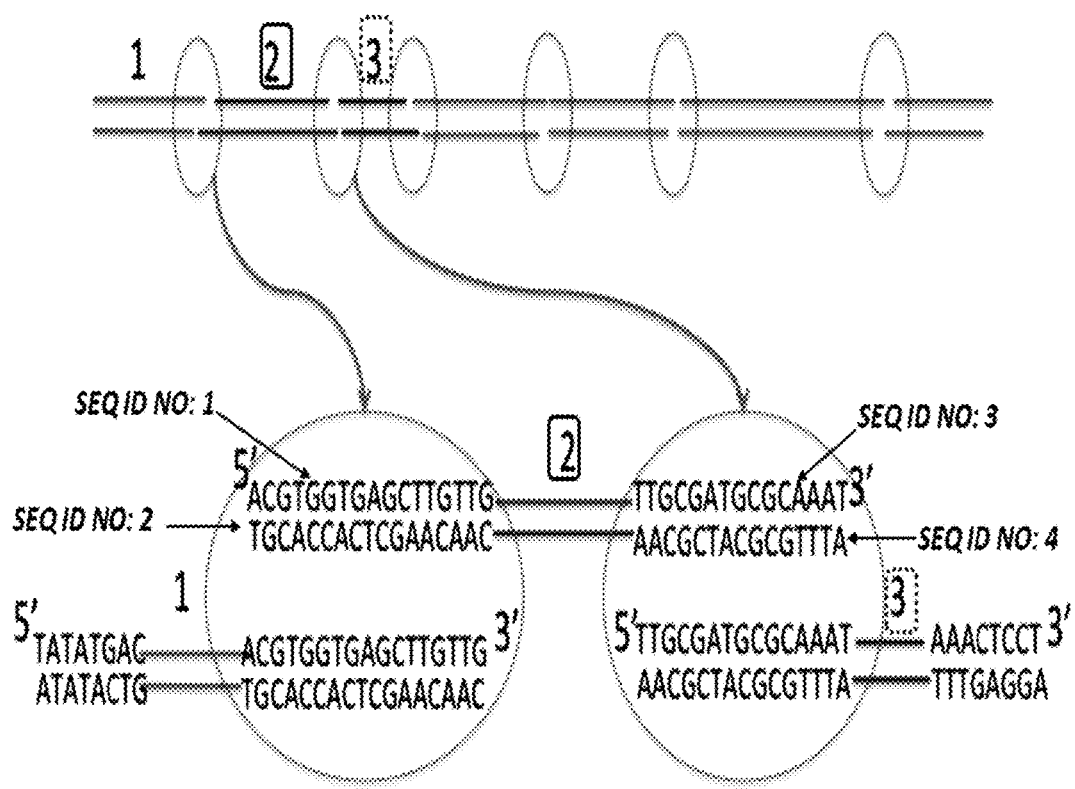
FIG. 1 is a schematic illustrating the method of the invention for creating duplicated sequence (linker sequences) on either end of DNA fragments that, when sequenced, facilitates the identification of their adjacent fragments. This method preserves linkage identity, enables haplotyping and facilitates de novo sequences assembly by contig joining (SEQ ID NOs: 1-4).

As described previously herein, the methods of the present invention include methods of fragmenting the whole genome so that the ends of the adjacent DNA fragments share common linker sequences. These linker sequences are normally 50 bases long or more. Three such DNA fragments are illustrated in (FIG. 1). The ends of fragment 2 share the same sequences with fragment 1 and fragment 3 respectively.

The linked DNA fragments are either circularized to form linked-paired-end sequencing library, and/or directly shotgun sequenced. In the case of the linked-paired-end sequencing library, additional 100-200 bases on both sides of the linker sequences (paired-end sequences), along with the linker sequences, are read with next generation sequencing technology (FIGS. 27A-27B). This sequencing information is used to construct a de novo whole genome map. This method will capture various scales of contiguity information at a throughput commensurate with the current scale of massively parallel sequencing, and extend the use of the short read sequencing technology in de novo genome assembly, structural variation detection, and haplotype-resolved genome sequencing. In the case of shotgun sequencing, the linked DNA fragments are shotgun sequenced by dilution, amplification, and the sequence reads can then be mapped back to the whole genome map, assembled with linked-paired-end sequencing library.

The linked-paired-end sequencing methods of the present invention offer a unique, high-throughput approach to address the main issues of short-read sequencing technology without introducing any additional equipment.

Based on linked-paired-end sequencing methods, the haplotype-scaffold sequencing (HSS) generates a haplotype-resolved scaffold, whose contiguity matches with shotgun, short reads contig size. This allows direct use for supporting de novo assembly of complex genomes. The HSS procedure can be easily integrated into standard sequencing protocol (e.g. Illumina sequencing). Since the methods of the invention relate only to sequencing a small portion of the genome, they do not add any significant cost to whole genome shotgun sequencing. The linked-paired-end sequencing libraries of the present invention can be run together with other shotgun sequencing libraries.

The methods of this invention rely on sequencing the DNA fragments generated at certain sequence motifs and provides more structured sequence contiguity than traditional mate-pair library, which relies on randomly sheared fragments and requires more coverage to provide full linkage. The procedures provided herein are much simpler than the stochastic separation of sequencing fragments, as they do not require thousands of pools and sequencing barcodes. Based on linked-paired-end libraries, the HSS generates internal barcodes (50-250 bp) between the sequencing fragments and thus provides higher resolution and more information content than classical genome mapping. Because the methods of the invention provide up 250 bp at sequence motif sites, instead of few bases as is the case in the genome mapping, denser nickases can be used because they will not limited by optical resolution.

In summary by using the methods of the present invention, high-quality, low-cost de novo assembly of complex genomes is made possible.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of generating a linked-paired-end nucleic acid fragment from a DNA sample, the method comprising:
   a. contacting a double-stranded DNA template having a first and a second DNA strand with a first nicking endonuclease to form a nick at a sequence-specific nicking location on the first DNA strand;
   b. conducting a base extension reaction on the first DNA strand along a corresponding region of the second DNA strand thereby forming a single-stranded flap on the double-stranded DNA template adjacent to the sequence-specific nicking location;
   c. contacting the double-stranded DNA template of b) with a second nicking endonuclease to form a cut at a sequence-specific location thereby generating two cut DNA fragments wherein the single stranded flap of b) can hybridize on the complementary strand of one of the two fragments of the cut DNA; and,
   d. conducting a base extension reaction on the second DNA strand of the other fragment of the cut DNA of c) along a corresponding region of the first DNA strand, wherein the reaction starts at the nick and progressing toward the 3' end of the first DNA strand thereby generating a double-stranded DNA fragment that shares common linker sequences with the double-stranded DNA fragment of c).

2. The method of claim 1, wherein the generated DNA fragments of d) are further processed further using hexamer extension.

3. The method of claim 1, wherein the first and second nicking endonucleases are type II endonucleases.

4. The method of claim 1, wherein the first and second nicking endonucleases comprise one or more endonucleases selected from the group consisting of Nb.BbvCI, Nb.BsmI, NbBsrDI, Nb.BtsI, Nt.AlwI, Nt.BbvCI, Nt.BsmAI, Nt.BspQI, Nt.BstNBI, and Nt.CviPII.

5. The method of claim 4, wherein the first nicking enzyme and the second nicking enzyme comprise at least one enzyme combination from the group consisting of Nt.BbvcI/Nb.BbvcI respectively and Nb.BbvcI/Nt.BbvcI respectively.

6. The method of claim 1, wherein the base extension reaction of b) comprises contacting the first DNA strand with a polymerase, one or more nucleotides, and a ligase.

7. The method of claim 1, wherein the generated fragments are 50 kb or less and the adjacent linker fragments share at least one selected from the group consisting of 100 bp or more and 50 bp or more.

8. The method of claim 1, wherein the linked-paired-end fragments are sequenced with at least one high throughput next generation sequencing platform selected from the group consisting of Illumina sequencing, SOLiD sequencing, 454 pyrosequencing and Ion Torrent semiconductor sequencing.

9. The method of claim 8, wherein the library preparation for sequencing comprises:
   a. circularizing the linked-paired-end fragments;
   b. fragmenting and size selecting the fragments of interest; and,
   c. ligating adaptors at a location selected from the group consisting of both ends of the fragments for paired-end sequencing and one end of the fragments for singled-end sequencing.

10. A method of generating a linked-paired-end nucleic acid fragment from a DNA sample, the method comprising:
    a. contacting a double-stranded DNA template having a first and a second DNA strand with a first nicking endonuclease to form a nick at a sequence-specific nicking location on the first DNA strand;
    b. conducting a base extension reaction on the first DNA strand along a corresponding region of the second DNA strand thereby forming a single-stranded flap on the double-stranded DNA template adjacent to the sequence-specific nicking location;
    c. contacting the double-stranded DNA template of b) with a second nicking endonuclease being a T7 endonuclease to generate a cut of the second DNA strand across the nicking sites thereby generating two cut DNA fragments: a first fragment with a blunt end and a second fragment with an overhang corresponding to the single stranded flap of b); and,
    d. conducting a base extension reaction on the second fragment with the flap overhang from c) wherein the based extension being along the corresponding region of the single stranded flap, and the reaction starting at the nick site of the T7 endonuclease and progressing toward the end of the stranded flap thereby generating a blunt end double-stranded DNA fragment that shares common linker sequences with the first double-stranded DNA fragment of c).

11. The method of claim 10, wherein the first nicking endonuclease is a type II endonuclease.

12. The method of claim 10, wherein the first nicking endonuclease comprises one or more endonucleases selected from the group consisting of Nb.BbvCI, Nt.BbvCI, Nt.BsmI, Nt.BsmAI, Nt.BstNBI, Nb.BsrDI, Nb.BstI, Nt.BspQI, Nt.Bpu10I and Nt.Bpu10I.

13. The method of claim 10, wherein the base extension reaction comprises contacting the first DNA strand with a polymerase, one or more nucleotides, and a ligase.

14. The method of claim 10, wherein the generated fragments are 50 kb or less and the adjacent linker fragments share at least one selected from the group consisting of 100 bp or more and 50 bp or more.

15. The method of claim 10, wherein the linked-paired-end fragments are sequenced with at least one high throughput next generation sequencing platform selected from the group consisting of Illumina sequencing, SOLiD sequencing, 454 pyrosequencing and Ion Torrent semiconductor sequencing.

16. The method of claim 15, wherein the library preparation for sequencing comprises:
    a. circularizing the linked-paired-end fragments;
    b. fragmenting and size selecting the fragments of interest; and,
    c. ligating adaptors at a location selected from the group consisting of both ends of the fragments for paired-end sequencing and one end of the fragments for singled-end sequencing.

* * * * *

SEQUENCE LISTING

```
<160> NUMBER OF SEQ ID NOS: 39

<210> SEQ ID NO 1
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 1
acgtggtgag cttgttg                                                    17
```

<210> SEQ ID NO 2
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 2
caacaagctc accacgt                                                    17

<210> SEQ ID NO 3
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 3
ttgcgatgcg caaat                                                      15

<210> SEQ ID NO 4
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 4
atttgcgcat cgcaa                                                      15

<210> SEQ ID NO 5
<211> LENGTH: 68
<212> TYPE: DNA
<213> ORGANISM: Artificial Sequence
<220> FEATURE:
<223> OTHER INFORMATION: Chemically Synthesized

<400> SEQUENCE: 5
tttcccaaat ttcccgggtt tcccaaaggg gctgaggctt taaagggttt cccgggaaag     60
ggccctttt                                                             68

<210> SEQ ID NO 6
<211> LENGTH: 68
<212> TYPE: DNA
<213> ORGANISM: Artificial Sequence
<220> FEATURE:
<223> OTHER INFORMATION: Chemically Synthesized

<400> SEQUENCE: 6
aaagggccct ttcccgggaa acctttaaa gcctcagccc ctttgggaaa cccgggaaat      60
ttgggaaa                                                              68

<210> SEQ ID NO 7
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 7
tttcccagct gaggccgggt ttccc                                           25

<210> SEQ ID NO 8

```
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 8
ggaaacccgg cctcagctgg gaaa                                              24

<210> SEQ ID NO 9
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 9 aaagggctg aggtttaaag ggtttcccgg gaaagggccc ttt                          43

<210> SEQ ID NO 10
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 10
aaagggccct ttcccgggaa acctttaaa cctcagcccc ttt                          43

<210> SEQ ID NO 11
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 11
cgctttccca cctcagcccg ggtttccc                                          28

<210> SEQ ID NO 12
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 12
gggaaacccg ggctgaggtg ggaaagcg                                          28

<210> SEQ ID NO 13
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 13
aaagggcctc agctttaaag ggtttcccgg gaaagggccc ttt                         43

<210> SEQ ID NO 14
<211> LENGTH: 43
<212> TYPE: DNA
<213> ORGANISM: Artificial Sequence
<220> FEATURE:
<223> OTHER INFORMATION: Chemically Synthesized

<400> SEQUENCE: 14
```

```
aaagggccct tcccgggaa acccttaaa gctgaggccc ttt          43
```

<210> SEQ ID NO 15
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 15

```
cgctttccca gctgaggccg ggtttccc                         28
```

<210> SEQ ID NO 16
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 16

```
gggaaacccg gcctcagctg ggaaagcg                         28
```

<210> SEQ ID NO 17
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 17

```
ggcccgactc cacccttt                                    18
```

<210> SEQ ID NO 18
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 18

```
aaaggctgag gtttaaaggg ttt                              23
```

<210> SEQ ID NO 19
<211> LENGTH: 12
<212> TYPE: DNA
<213> ORGANISM: Artificial Sequence
<220> FEATURE:
<223> OTHER INFORMATION: Chemically Synthesized

<400> SEQUENCE: 19

```
cctcagccct tt                                          12
```

<210> SEQ ID NO 20
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 20

```
tgaggccggg tttcc                                       15
```

<210> SEQ ID NO 21
<211> LENGTH: 13
<212> TYPE: DNA

```
<213> ORGANISM: Artificial Sequence
<220> FEATURE:
<223> OTHER INFORMATION: Chemically Synthesized

<400> SEQUENCE: 21
ggaaaccccg gcc                                                              13

<210> SEQ ID NO 22
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 22 aaagggctg aggtttaaag ggttt                                                  25

<210> SEQ ID NO 23
<211> LENGTH: 13
<212> TYPE: DNA
<213> ORGANISM: Artificial Sequence
<220> FEATURE:
<223> OTHER INFORMATION: Chemically Synthesized

<400> SEQUENCE: 23
cctcagccct ttg                                                              13

<210> SEQ ID NO 24
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 24
tgaggccggg tttccc                                                           16

<210> SEQ ID NO 25
<211> LENGTH: 11
<212> TYPE: DNA
<213> ORGANISM: Artificial Sequence
<220> FEATURE:
<223> OTHER INFORMATION: Chemically Synthesized

<400> SEQUENCE: 25
tttcccggag t                                                                11

<210> SEQ ID NO 26
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 26
tcagcccggg tttccc                                                           16

<210> SEQ ID NO 27
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 27
cctttgggcc cgactccacc cttt                                                  24
```

```
<210> SEQ ID NO 28
<211> LENGTH: 11
<212> TYPE: DNA
<213> ORGANISM: Artificial Sequence
<220> FEATURE:
<223> OTHER INFORMATION: Chemically Synthesized

<400> SEQUENCE: 28
actccgggaa a                                                            11

<210> SEQ ID NO 29
<211> LENGTH: 15
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (6)..(15)
<223> OTHER INFORMATION: n is a, c, g, or t

<400> SEQUENCE: 29
gacgcnnnnn nnnnn                                                        15

<210> SEQ ID NO 30
<211> LENGTH: 15
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(10)
<223> OTHER INFORMATION: n is a, c, g, or t

<400> SEQUENCE: 30
nnnnnnnnnn gcgtc                                                        15

<210> SEQ ID NO 31
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 31
gtgatataat gctat                                                        15

<210> SEQ ID NO 32
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 32
acgtggtgaa cgtgga                                                       16

<210> SEQ ID NO 33
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 33
```
cgtggaatgc ttgttg                                                    16

<210> SEQ ID NO 34
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 34
ttgcgatggc ttgagc                                                    16

<210> SEQ ID NO 35
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 35
gcttgagccg caaat                                                     15

<210> SEQ ID NO 36
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 36
ccttttttcc cagagtcggc cgggtttccc                                     30

<210> SEQ ID NO 37
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 37
gggaaacccg gccgactctg ggaaaaaagg                                     30

<210> SEQ ID NO 38
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 38 aaagggact tggtttaaag ggtttcccgg                                      30

<210> SEQ ID NO 39
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 39
ccgggaaacc ctttaaacca agtccccttt                                     30